(12) United States Patent
Bechtel et al.

(10) Patent No.: US 10,849,536 B2
(45) Date of Patent: Dec. 1, 2020

(54) DETERMINING ABSOLUTE AND RELATIVE TISSUE OXYGEN SATURATION

(71) Applicant: ViOptix, Inc., Newark, CA (US)

(72) Inventors: Kate LeeAnn Bechtel, Pleasant Hill, CA (US); Robert Lohman, Buffalo, NY (US); Risal Djohan, Westlake, OH (US); Scott Coleridge, Belle Mead, NJ (US)

(73) Assignee: ViOptix, Inc., Newark, CA (US)

( * ) Notice: Subject to any disclaimer, the term of this patent is extended or adjusted under 35 U.S.C. 154(b) by 594 days.

(21) Appl. No.: 15/495,212

(22) Filed: Apr. 24, 2017

(65) Prior Publication Data

US 2017/0303837 A1   Oct. 26, 2017

Related U.S. Application Data

(60) Provisional application No. 62/326,673, filed on Apr. 22, 2016, provisional application No. 62/326,644, (Continued)

(51) Int. Cl.
*A61B 5/1455* (2006.01)
*A61B 5/00* (2006.01)

(52) U.S. Cl.
CPC ........ *A61B 5/14552* (2013.01); *A61B 5/4848* (2013.01); *A61B 5/7221* (2013.01);
(Continued)

(58) Field of Classification Search
CPC ... A61B 5/145; A61B 5/1455; A61B 5/14551; A61B 5/14552; A61B 5/743;
(Continued)

(56) References Cited

U.S. PATENT DOCUMENTS 6,385,821 B1   5/2002   Modgil et al.
7,236,813 B2   6/2007   Parker
(Continued)

FOREIGN PATENT DOCUMENTS

EP   0102816       3/1984
EP   0102816 A2    3/1984
(Continued)

OTHER PUBLICATIONS

International Search Report, PCT Application PCT/US2017/029221, dated Jul. 30, 2017, 5 pages.
(Continued)

*Primary Examiner* — Eric F Winakur
*Assistant Examiner* — Chu Chuan Liu
(74) *Attorney, Agent, or Firm* — Aka Chan LLP

(57) ABSTRACT

An oximeter probe is user configurable for being in an absolute reporting mode and a relative reporting mode for measured values. The measured values for the absolute and relative modes include absolute oxygen saturation, relative oxygen saturation, absolute hemoglobin content, relative hemoglobin content, absolute blood volume, relative blood volume. The relative modes and absolute modes for determining and reporting relative or absolute hemoglobin content or relative or absolute blood volume for individual patients are beneficial when determining the efficacy of administered medications, such as epinephrine, that effect blood flow, but not oxygen saturation, in tissue, such as skin. The oximeter probe in these relative modes displays the efficacy of the administered medication as reported values for relative hemoglobin content or relative blood volume fall or rise.

20 Claims, 24 Drawing Sheets

Related U.S. Application Data filed on Apr. 22, 2016, provisional application No. 62/326,630, filed on Apr. 22, 2016.

(52) U.S. Cl.
CPC ............ *A61B 5/7275* (2013.01); *A61B 5/742* (2013.01); *A61B 5/743* (2013.01); *A61B 5/7475* (2013.01); *A61B 2560/0214* (2013.01); *A61B 2560/0425* (2013.01); *A61B 2560/0475* (2013.01); *A61B 2562/0238* (2013.01); *A61B 2562/0242* (2013.01); *A61B 2562/046* (2013.01)

(58) Field of Classification Search
CPC ... A61B 5/7475; A61B 5/4848; A61B 5/7221; A61B 5/7275; A61B 5/742; A61B 2562/0242; A61B 2562/04; A61B 2562/046
See application file for complete search history.

(56) References Cited

U.S. PATENT DOCUMENTS

| | | | |
|---|---|---|---|
| 7,860,554 | B2 | 12/2010 | Leonardi et al. |
| 8,233,955 | B2 | 7/2012 | Al-ali et al. |
| 8,622,918 | B1 | 1/2014 | Mao et al. |
| 8,938,279 | B1 | 1/2015 | Heaton, II et al. |
| 2003/0009092 | A1 | 1/2003 | Parker |
| 2004/0034294 | A1 | 2/2004 | Kimball et al. |
| 2006/0053522 | A1 | 3/2006 | Kimbell |
| 2007/0244377 | A1 | 10/2007 | Cozad et al. |
| 2008/0319290 | A1 | 12/2008 | Mao et al. |
| 2009/0253968 | A1 | 10/2009 | Cho et al. |
| 2010/0005630 | A1 | 1/2010 | Gitman et al. |
| 2010/0099964 | A1* | 4/2010 | O'Reilly ............ A61B 5/14546 600/323 |
| 2010/0292549 | A1 | 11/2010 | Shuler |
| 2010/0298728 | A1 | 11/2010 | Addison et al. |
| 2011/0205535 | A1 | 8/2011 | Soller et al. |
| 2011/0224518 | A1 | 9/2011 | Tindi et al. |
| 2011/0276276 | A1 | 11/2011 | Kashyap et al. |
| 2012/0289801 | A1 | 11/2012 | Yamaguchi |
| 2013/0023743 | A1 | 1/2013 | Al-ali et al. |
| 2013/0225952 | A1* | 8/2013 | Lin ................... A61B 5/14552 600/323 |
| 2013/0317331 | A1 | 11/2013 | Bechtel et al. |
| 2014/0031628 | A1 | 1/2014 | Kaku |
| 2014/0046152 | A1 | 2/2014 | Bechtel et al. |
| 2014/0180043 | A1 | 6/2014 | Addison et al. |
| 2014/0288386 | A1 | 9/2014 | Zand et al. |
| 2015/0099955 | A1* | 4/2015 | Al-Ali ................. A61B 5/1455 600/364 |
| 2015/0257690 | A1* | 9/2015 | Su ..................... A61B 5/14552 600/324 |

FOREIGN PATENT DOCUMENTS

| | | |
|---|---|---|
| EP | 1889569 | 6/2014 |
| EP | 1889569 B1 | 6/2014 |
| WO | 2009090665 | 7/2009 |
| WO | 2009090665 A1 | 7/2009 |
| WO | 2010011763 | 1/2010 |
| WO | 2010042264 | 4/2010 |
| WO | 2010042264 A1 | 4/2010 |
| WO | 2014026200 | 2/2014 |

OTHER PUBLICATIONS

Chen, Tong et al., Detection of Psychological Stress Using a Hyperspectral Imaging Technique, IEEE Transactions on Affective Computing, Oct. 9, 2014, pp. 391-405, vol. 5, No. 4, Oct.-Dec. 2014, IEEE.

European Patent Office, Extended European Search Report, EP Application No. 17786813.0, dated Nov. 12, 2019, 13 pages.

\* cited by examiner

DETERMINING ABSOLUTE AND RELATIVE TISSUE OXYGEN SATURATION

CROSS-REFERENCE TO RELATED APPLICATIONS

This application claims the benefit of the following U.S. patent applications 62/326,630, 62/326,644, and 62/326,673, filed Apr. 22, 2016. These applications are incorporated by reference along with all other references cited in these applications.

BACKGROUND OF THE INVENTION

The present invention relates generally to optical systems that monitor oxygen levels in tissue. More specifically, the present invention relates to optical probes, such as oximeters, that include sources and detectors on sensor heads of the optical probes and that use locally stored simulated reflectance curves for determining oxygen saturation of tissue.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these measurements.

In particular, assessing a patient's oxygenation state, at both the regional and local level, is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of non-ideal conditions. While existing oximeters have been sufficient for post-operative tissue monitoring where absolute accuracy is not critical and trending data alone is sufficient, accuracy is, however, required during surgery in which spot-checking can be used to determine whether tissue might remain viable or needs to be removed.

Therefore, there is a need for improved tissue oximeter probes and methods of making measurements using these probes.

BRIEF SUMMARY OF THE INVENTION

An oximeter probe utilizes a relatively large number of simulated reflectance curves to quickly determine the optical properties of tissue under investigation. The optical properties of the tissue allow for the further determination of the oxygenated hemoglobin and deoxygenated hemoglobin concentrations of the tissue as well as the oxygen saturation of the tissue.

In one implementation, the oximeter probe can measure oxygen saturation without requiring a pulse or heart beat. An oximeter probe of the invention is applicable to many areas of medicine and surgery including plastic surgery. The oximeter probe can make oxygen saturation measurements of tissue where there is no pulse. Such tissue may have been separated from the body (e.g., a flap) and will be transplanted to another place in the body. Aspects of the invention may also be applicable to a pulse oximeter. In contrast to an oximeter probe, a pulse oximeter requires a pulse in order to function. A pulse oximeter typically measures the absorption of light due to the pulsing arterial blood.

In an implementation, relative values of oxygenation measurement, such as relative oxygen saturation measurements are determined and display so that uses of the oximeter probe can determine the effectiveness of administered medications that effect oxygen saturation over time, such as epinephrine or other medications.

In an implementation a method includes contacting a probe tip to a target tissue of a patient; transmitting first light at a first time from a source structure of the oximeter probe into the target tissue; detecting first reflected light that is reflected from the target tissue by a plurality of detector structures of the oximeter probe; generating by the detector structures first reflectance data for the first reflected light detected by the detector structures; fitting the reflectance data to a plurality of simulated reflectance curves; determining one or more best fitting ones of the simulated reflectance curves from the fit of the first reflectance data to the plurality of simulated reflectance curves, where each of the simulated reflectance curves is associated with a value for an absorption coefficient; determining at least a first absorption coefficients for the one or more best fitting ones of the simulated reflectance curves to the first reflectance data; determining a first value for a first oxygen saturation based on the first absorption coefficient; and storing the first value for the first oxygen saturation in the memory.

The method includes transmitting second light at a second time from the source structure of the oximeter probe into the target tissue; detecting second reflected light that is reflected from the target tissue by the plurality of detector structures of the oximeter probe; generating by the detector structures second reflectance data for the second reflected light detected by the detector structures; fitting the second reflectance data to the plurality of simulated reflectance curves; determining one or more best fitting ones of the simulated reflectance curves from the fit of the second reflectance data to the plurality of simulated reflectance curves; determining at least a second absorption coefficients for the one or more best fitting ones of the simulated reflectance curves to the second reflectance data; determining a second value for a second oxygen saturation based on the second absorption coefficient.

The method includes retrieving the first value from the memory; determining a percentage difference between the first and second value; and displaying the percentage difference on a display of the oximeter probe.

In an implementation, a system includes an oximeter device comprising a probe tip comprises source structures and detector structures on a distal end of the device and a display proximal to the probe tip, where the oximeter device calculates an first oxygen saturation value, second oxygen saturation value, and relative oxygen saturation value between the first and second oxygen saturation values, and displays the relative oxygen saturation value between the first and second oxygen saturation values, and the oximeter device is specially configured to: at a first time period, transmit light from a light source of an oximeter probe into a first tissue to be measured; receive light at a detector of the oximeter probe that is reflected by the first tissue in response to the transmitted light at the first time period; at a second time period, transmit light from the light source of the oximeter probe into a second tissue to be measured, where the second time period is after the first time period; receive light at the detector of the oximeter probe that is reflected by the second tissue in response to the transmitted light at the second time period; determine the first oxygen saturation value for the first tissue; determine the second oxygen saturation value for the second tissue; calculate a relative oxygen saturation value between the first and second oxygen saturation values; and display the relative oxygen saturation value on the display.

A system includes an oximeter probe comprising: a handheld housing; a processor housed in the handheld housing; a memory, housed in the handheld housing, electronically coupled to the processor and storing first code for controlling the processor; a display, accessible from an exterior of the handheld housing, electronically coupled to the processor; and a battery, housed in the handheld housing, coupled to and supplies power to the processor, the memory, and the display.

The code includes instruction executable by the processor for: controlling at a first time a source structure of the oximeter probe to emit first light into target tissue of a patient; controlling detection by a plurality of detector structures of the oximeter probe of first reflected light that is reflected from the target tissue; receiving from the detector structures first reflectance data generated by the detector structures for the first reflected light detected by the detector structures; fitting the reflectance data to a plurality of simulated reflectance curves; determining one or more best fitting ones of the simulated reflectance curves from the fit of the first reflectance data to the plurality of simulated reflectance curves, where each of the simulated reflectance curves is associated with a value for an absorption coefficient; determining at least a first absorption coefficients for the one or more best fitting ones of the simulated reflectance curves to the first reflectance data; determining a first value for a first oxygen saturation based on the first absorption coefficient; and storing the first value for the first oxygen saturation in the memory.

The code includes instruction executable by the processor for controlling at a second time the source structure of the oximeter probe to emit second light into the target tissue; detecting second reflected light that is reflected from the target tissue by the plurality of detector structures of the oximeter probe; generating by the detector structures second reflectance data for the second reflected light detected by the detector structures; fitting the second reflectance data to the plurality of simulated reflectance curves; determining one or more best fitting ones of the simulated reflectance curves from the fit of the second reflectance data to the plurality of simulated reflectance curves; determining at least a second absorption coefficients for the one or more best fitting ones of the simulated reflectance curves to the second reflectance data; determining a second value for a second oxygen saturation based on the second absorption coefficient.

The code includes instruction executable by the processor for retrieving the first value from the memory; determining a percentage difference between the first and second value; and controlling display of the percentage difference on a display of the oximeter probe.

In an implementation a method includes contacting a probe tip to a target tissue of a patient; transmitting first light at a first time from a source structure of the oximeter probe into the target tissue; detecting first reflected light that is reflected from the target tissue by a plurality of detector structures of the oximeter probe; generating by the detector structures first reflectance data for the first reflected light detected by the detector structures; fitting the reflectance data to a plurality of simulated reflectance curves; determining one or more best fitting ones of the simulated reflectance curves from the fit of the first reflectance data to the plurality of simulated reflectance curves, where each of the simulated reflectance curves is associated with a value for an absorption coefficient; determining at least a first absorption coefficients for the one or more best fitting ones of the simulated reflectance curves to the first reflectance data; determining a first value for a first tissue measurement based on the first absorption coefficient; and storing the first value for the tissue measurement in the memory.

The method includes transmitting second light at a second time from the source structure of the oximeter probe into the target tissue; detecting second reflected light that is reflected from the target tissue by the plurality of detector structures of the oximeter probe; generating by the detector structures second reflectance data for the second reflected light detected by the detector structures; fitting the second reflectance data to the plurality of simulated reflectance curves; determining one or more best fitting ones of the simulated reflectance curves from the fit of the second reflectance data to the plurality of simulated reflectance curves; determining at least a second absorption coefficients for the one or more best fitting ones of the simulated reflectance curves to the second reflectance data; and determining a second value for a second tissue measurement based on the second absorption coefficient.

The method includes retrieving the first value from the memory; determining a percentage difference between the first and second tissue measurements; and displaying the percentage difference between the first and second tissue measurements on a display of the oximeter probe.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 9 shows a table for a database for a homogeneous model of tissue of simulated reflectance curves that is stored in the memory of the oximeter probe in an implementation.

FIG. 10 shows a table for a database for a layered model of tissue of simulated reflectance curves that is stored in the memory of the oximeter probe in an implementation.

FIGS. 11A-11B show a table for a database for a layered model of tissue where each row in the database is for four simulated reflectance curves for the four wavelengths of light emitted from the simulated source structures and detected by the simulated detector structures.

DETAILED DESCRIPTION OF THE INVENTION

Figure 1:
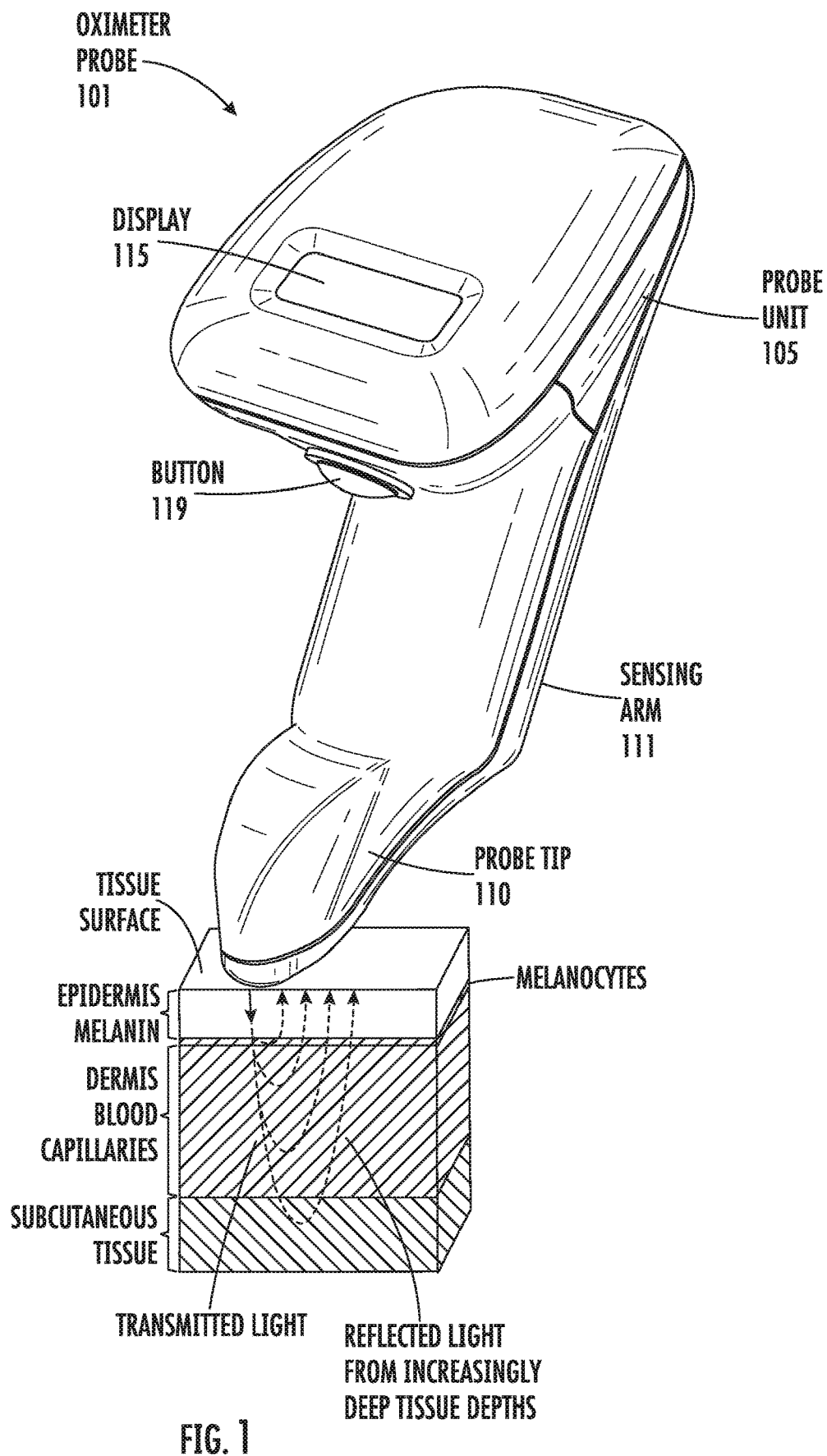
FIG. 1 shows an implementation of an oximeter probe.

FIG. 1 shows an image of an oximeter probe 101 in an implementation. Oximeter probe 101 is configured to make tissue oximetry measurements, such as intraoperatively and postoperatively. Oximeter probe 101 may be a handheld device that includes a probe unit 105, probe tip 110 (also referred to as a sensor head), which may be positioned at an end of a sensing arm 111. Oximeter probe 101 is configured to measure the oxygen saturation of tissue by emitting light, such as near-infrared light, from probe tip 110 into tissue, and collecting light reflected from the tissue at the probe tip.

Oximeter probe 101 includes a display 115 or other notification device that notifies a user of oxygen saturation measurements made by the oximeter probe. While probe tip 110 is described as being configured for use with oximeter probe 101, which is a handheld device, probe tip 110 may be used with other oximeter probes, such as a modular oximeter probe where the probe tip is at the end of a cable device that couples to a base unit. The cable device might be a disposable device that is configured for use with one patient and the base unit might be a device that is configured for repeated use. Such modular oximeter probes are well understood by those of skill in the art and are not described further.

Figure 2:
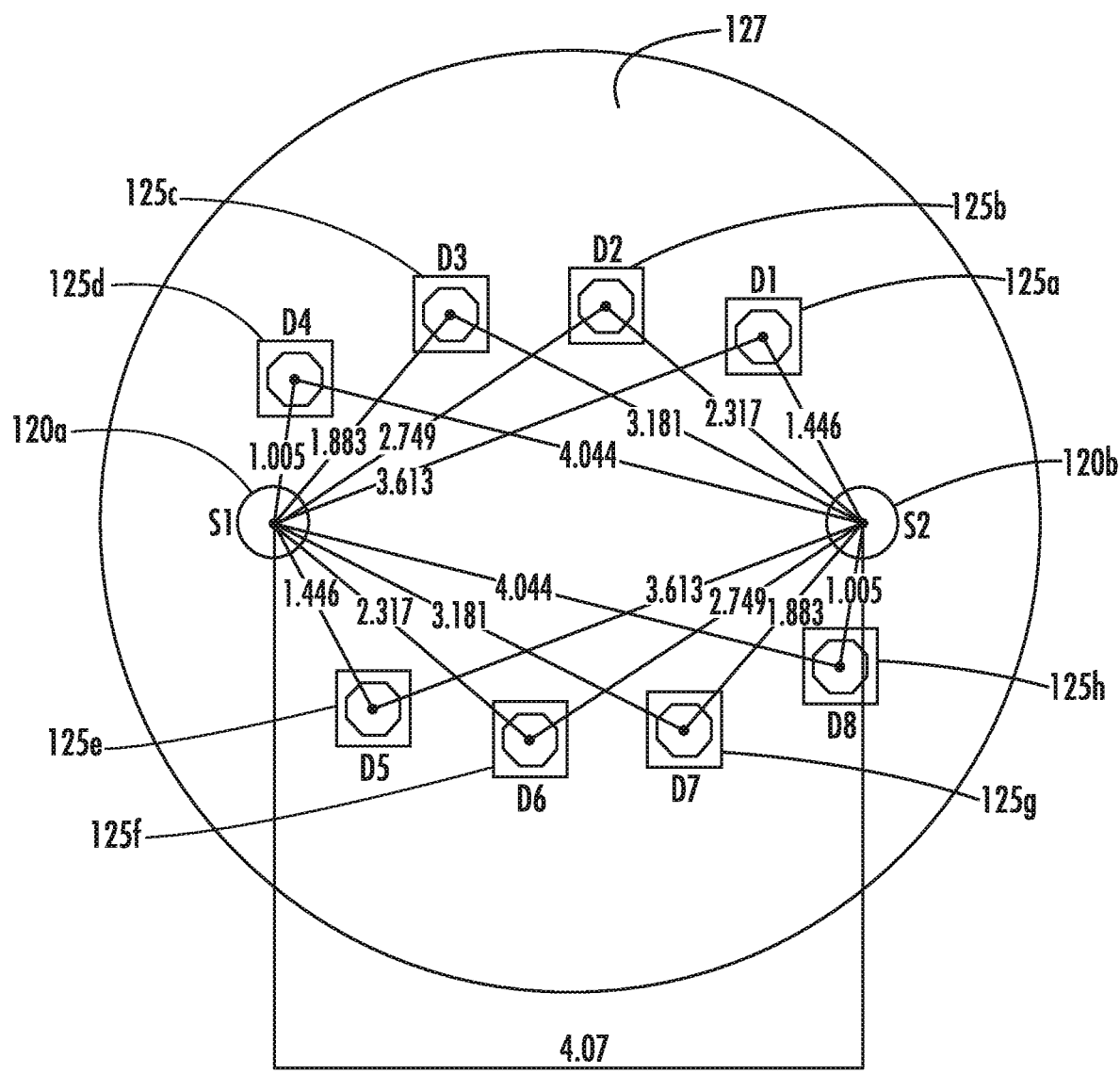
FIG. 2 shows an end view of the probe tip in an implementation.

FIG. 2 shows an end view of probe tip 110 in an implementation. Probe tip 110 is configured to contact tissue (e.g., a patient's skin) for which a tissue oximetry measurement is to be made. Probe tip 110 includes first and second source structures 120a and 120b (generally source structures 120) and includes first, second, third, fourth, fifth, sixth, seventh, and eighth detector structures 125a-125h (generally detector structures 125). In alternative implementations, the oximeter probe includes more or fewer source structures, includes more or fewer detector structures, or both.

Each source structure 120 is adapted to emit light (such as infrared light) and includes one or more light sources, such as four light sources that generate the emitted light. Each light source can emit one or more wavelengths of light. Each light source can include a light emitting diode (LED), a laser diode, an organic light emitting diode (OLED), a quantum dot LED (QMLED), or other types of light sources.

Each source structure can include one or more optical fibers that optically link the light sources to a face 127 of the probe tip. In an implementation, each source structure includes four LEDs and includes a single optical fiber that optically couples the four LEDs to the face of the probe tip. In alternative implementations, each source structure includes more than one optical fiber (e.g., four optical fibers) that optically couples the LEDs to the face of the probe tip.

Each detector structure includes one or more detectors. In an implementation, each detector structure includes a single detector adapted to detect light emitted from the source structures and reflected from tissue. The detectors can be photodetectors, photoresistors, or other types of detectors. The detector structures are positioned with respect to the source structures such that two or more (e.g., eight) unique source-to-detector distances are created.

In an implementation, the shortest source-to-detector distances are approximately equal. For example, the shortest source-to-detector distances are approximately equal between source structure 120a and detector structure 125d (S1-D4) and between source structure 120b and detector structure 125a (S2-D8) are approximately equal. The next longer source-to-detector distances (e.g., longer than each of S1-D4 and S2-D8) between source structure 120a and detector structure 125e (S1-D5) and between source structure 120b and detector structure 125a (S2-D1) are approximately equal. The next longer source-to-detector distances (e.g., longer than each of S1-D5 and S2-D1) between source structure 120a and detector structure 125c (S1-D3) and between source structure 120b and detector structure 125g (S2-D7) are approximately equal. The next longer source-to-detector distances (e.g., longer than each of S1-D3 and S2-D7) between source structure 120a and detector structure 125f (S1-D6) and between source structure 120b and detector structure 125b (S2-D2) are approximately equal. The next longer source-to-detector distances (e.g., longer than each of S1-D6 and S2-D2) between source structure 120a and detector structure 125c (S1-D2) and between source structure 120b and detector structure 125f (S2-D6) are approximately equal. The next longer source-to-detector distances (e.g., longer than each of S1-D2 and S2-D6) between source structure 120a and detector structure 125g (S1-D7) and between source structure 120b and detector structure 125c (S2-D3) are approximately equal. The next longer source-to-detector distances (e.g., longer than each of S1-D7 and S2-D3) between source structure 120a and detector structure 125a (S1-D1) and between source structure 120b and detector structure 125e (S2-D5) are approximately equal. The next longer source-to-detector distances (e.g., longest source-to-detector distance, longer than each of S1-D1 and S2-D5) between source structure 120a and detector structure 125h (S1-D8) and between source structure 120b and detector structure 125d (S2-D4) are approximately equal. In other implementations, the source-to-detector distance can all be unique or have fewer then eight distances that are approximately equal.

Table 1 below shows the eight unique source-to-detector distances according to an implementation. The increase between nearest source-to-detector distances is approximately 0.4 millimeters.

TABLE 1

| Source-to-Detector Pairs | Source-to-Detector Distances Millimeters |
|---|---|
| (S1-D4) | 1.005 |
| (S2-D8) | 1.005 |
| (S1-D5) | 1.446 |
| (S2-D1) | 1.446 |
| (S1-D3) | 1.883 |
| (S2-D7) | 1.883 |
| (S1-D6) | 2.317 |
| (S2-D2) | 2.317 |
| (S1-S2) | 2.749 |
| (S1-S2) | 2.749 |
| (S1-D7) | 3.181 |
| (S2-D3) | 3.181 |
| (S1-D1) | 3.613 |
| (S2-D5) | 3.613 |
| (S1-D8) | 4.004 |
| (S2-D4) | 4.004 |

In an implementation, for each wavelength of light (e.g., two, three, four, or more wavelengths of light in the visible spectrum, such as red, IR, or both visible and IR) that the oximeter probe is configured to emit, the oximeter probe includes at least two source-detector distances that are less than approximately 1.5 millimeters, less than approximately 1.6 millimeters, less than approximately 1.7 millimeters, less than approximately 1.8 millimeters, less than approximately 1.9 millimeters, or less than approximately 2.0 millimeters, and two source-detector distances that are greater than approximately 2.5 millimeters and less than approximately 4 millimeters, less than approximately 4.1 millimeters, less than approximately 4.2 millimeters, less than approximately 4.3 millimeters, less than approximately 4.4 millimeters, less than approximately 4.5 millimeters, less than approximately 4.6 millimeters, less than approximately 4.7 millimeters, less than approximately 4.8 millimeters, less than approximately 4.95 millimeters, or less than approximately 5 millimeters.

In an implementation, detector structures 125a and 125e are symmetrically positioned about a point that is on a straight line connecting sources 120a and 120b. Detector structures 125b and 125f are symmetrically positioned about the point. Detector structures 125c and 125g are symmetrically positioned about the point. Detector structures 125d and 125h are symmetrically positioned about the point. The point can be centered between source structures 120a and 120b on the connecting line.

A plot of source-to-detector distance verses reflectance detected by detector structures 125 can provide a reflectance curve where the data points are well spaced along the x-axis. These spacings of the distances between source structures 120a and 120b, and detector structures 125 reduces data redundancy and can lead to the generation of relatively accurate reflectance curves.

In an implementation, the source structures and detector structures can be arranged at various positions on the probe surface to give the distances desired (such as indicated above). For example, the two sources form a line, and there will be equal number of detectors above and below this line. And the position of a detector (above the line) will have point symmetry with another detector (below the line) about a selected point on the line of the two sources. As an example, the selected point may be the middle between the two sources, but not necessarily. In other implements, the positioning can be arranged based on a shape, such as a circle, an ellipse, an ovoid, randomly, triangular, rectangular, square, or other shape.

The following patent applications describe various oximeter devices and oximetry operation, and discussion in the following applications can be combined with aspects of the invention described in this application, in any combination. The following patent application are incorporated by reference along with all references cited in these application Ser. No. 14/944,139, filed Nov. 17, 2015, Ser. No. 13/887,130 filed May 3, 2013, Ser. No. 15/163,565, filed May 24, 2016, Ser. No. 13/887,220, filed May 3, 2013, Ser. No. 15/214,355, filed Jul. 19, 2016, Ser. No. 13/887,213, filed May 3, 2013, Ser. No. 14/977,578, filed Dec. 21, 2015, Ser. No. 13/887,178, filed Jun. 7, 2013, Ser. No. 15/220,354, filed Jul. 26, 2016, Ser. No. 13/965,156, filed Aug. 12, 2013, Ser. No. 15/359,570, filed Nov. 22, 2016, Ser. No. 13/887,152, filed May 3, 2013, Ser. No. 29/561,749, filed Apr. 16, 2016, 61/642,389, 61/642,393, 61/642,395, 61/642,399, filed May 3, 2012, 61/682,146, filed Aug. 10, 2012, Ser. Nos. 15/493,132, 15/493,111, 15/493,121, filed Apr. 20, 2017, Ser. No. 15/494,444, filed Apr. 21, 2017, Ser. Nos. 15/495,194, 15/495,205, and 15/495,212, filed Apr. 24, 2017.

Figure 3:
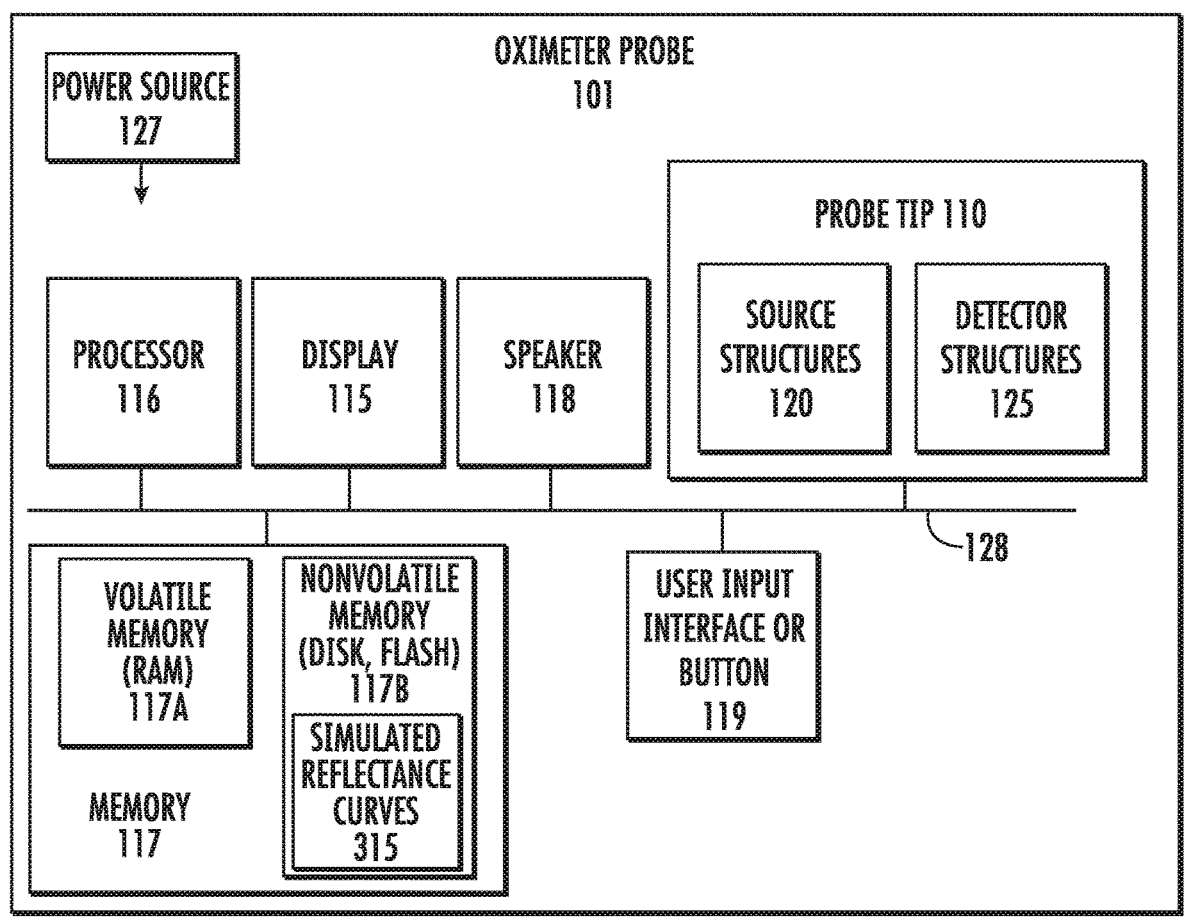
FIG. 3 shows a block diagram of an oximeter probe.

FIG. 3 shows a block diagram of oximeter probe 101 in an implementation. Oximeter probe 101 includes display 115, a processor 116, a memory 117, a speaker 118, one or more user-selection devices 119 (e.g., one or more buttons, switches, touch input device associated with display 115), a set of source structures 120, a set of detector structures 125, and a power source (e.g., a battery) 127. The foregoing listed components may be linked together via a bus 128, which may be the system bus architecture of oximeter probe 101. Although this figure shows one bus that connects to each component, the busing is illustrative of any interconnection scheme serving to link these components or other components included in oximeter probe 101. For example, speaker 118 could be connected to a subsystem through a port or have an internal direct connection to processor 116. Further, the components described are housed in a mobile housing (see FIG. 1) of oximeter probe 101 in an implementation.

Processor 116 may include a microprocessor, a microcontroller, a multicore processor, or other processor type. Memory 117 may include a variety of memories, such as a volatile memory 117a (e.g., a RAM), a nonvolatile memory 117b (e.g., a disk or FLASH). Different implementations of oximeter probe 101 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the handheld device for several hours. In an implementation, the oximeter probe is a disposable.

In other implementations, the battery is rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Figure 4A:
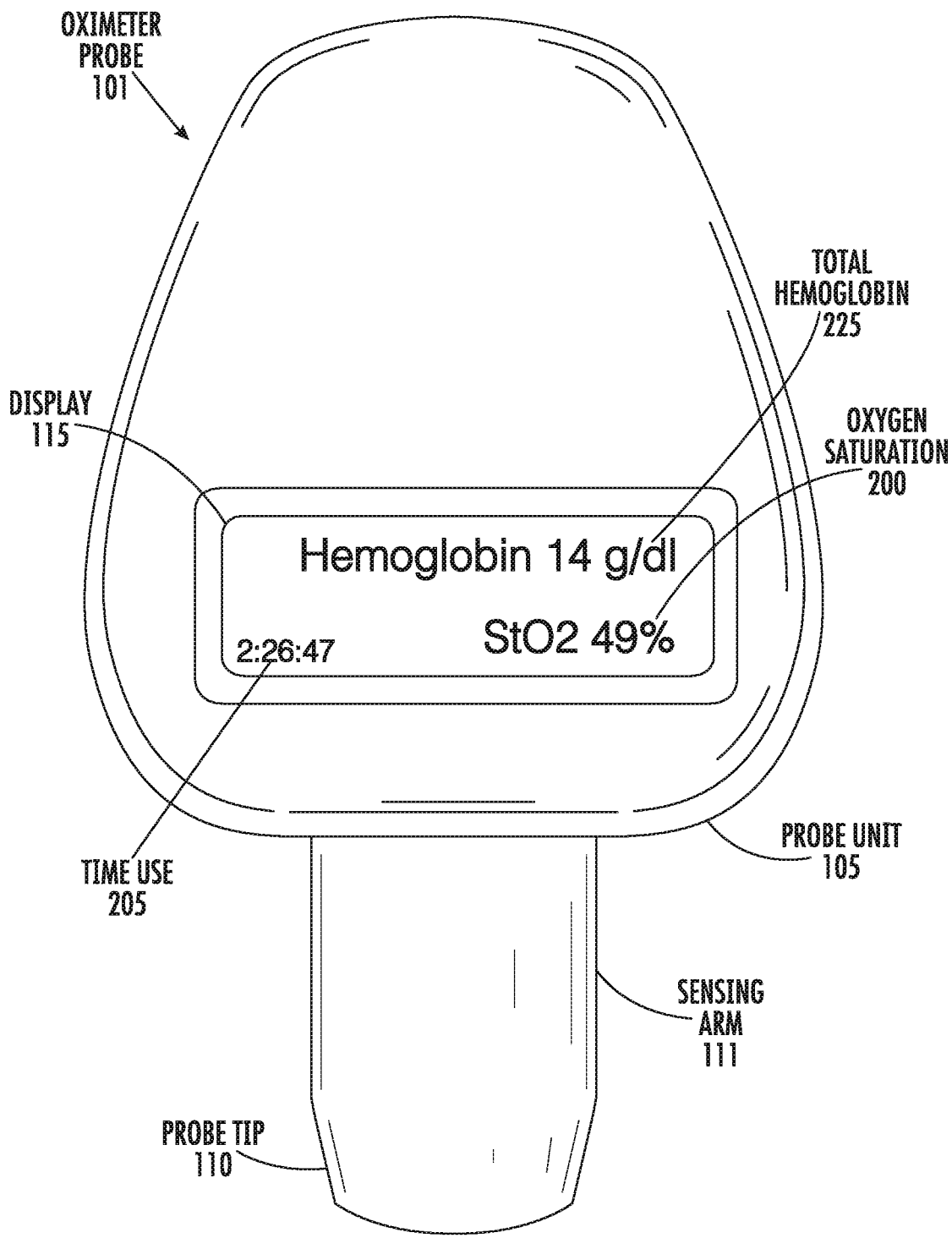
FIG. 4A shows a top view of the oximeter probe in an implementation where the display is adapted to display a value for the oxygen saturation and a value for the total hemoglobin.
Figure 4B:
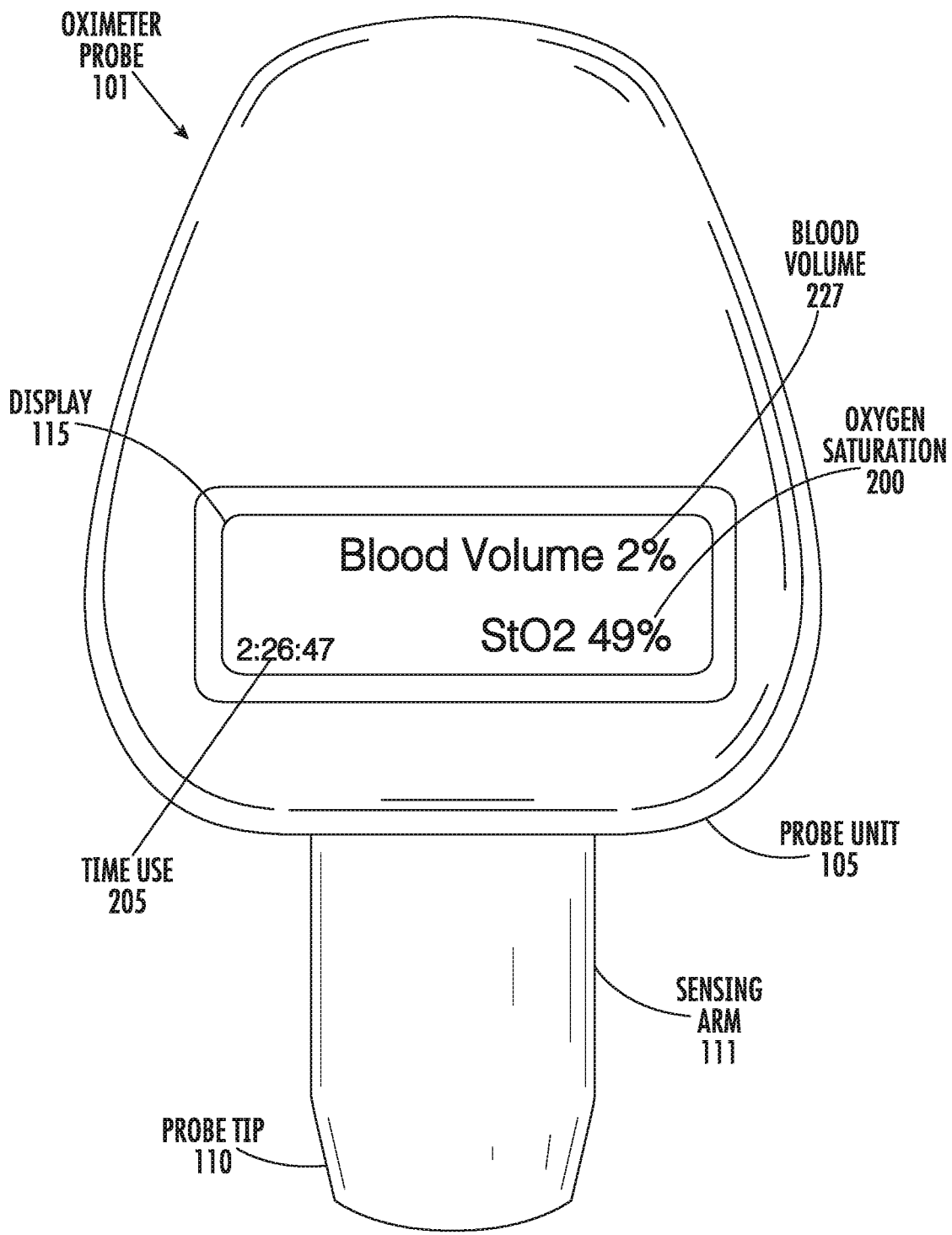
FIG. 4B shows a top view of the oximeter probe in an implementation where the display is adapted to display a value for the oxygen saturation and a value for the blood volume.

FIGS. 4A and 4B show top views of the oximeter probe 101 in an implementation. The top view shows the display 115 located in the probe unit 105 at a top portion of the oximeter probe. The display is adapted to display one or more pieces of information regarding the oximeter probe and measurement information for measurements made by the probe.

In an implementation, the display is adapted to display a value for the oxygen saturation 200 ("oxygen saturation value") of tissue that is measured by the oximeter probe. The display can display the oxygen saturation as a percentage value, a bar graph with a number of bars, via one or more colors (e.g., if the display is a color display), or with other displayable information.

The display can also be adapted to display a value 205 for the duration for which the oximeter probe has been operating, for example, since a reset. The reset of the oximeter probe can occur when the batteries in the probe are changed, from a first power up on a previously unused set of batteries (fresh batteries), since a power up from a hard power down, since a power up from a soft power down (e.g., a hibernation mode), or other reset event.

The display can display a value for the total hemoglobin per blood volume 225 (FIG. 4A) or display a value for the blood volume (e.g., percentage of blood per volume of tissue probed, FIG. 4B). Determination of total hemoglobin and the blood volume by the oximeter probe are described below. In an implementation, the displayed value for melanin is a value (e.g., an indexed value) that representing the hemoglobin concentration, such the hemoglobin concentration in the volume of tissue being sampled where this value may be a unitless value.

Figure 4C:
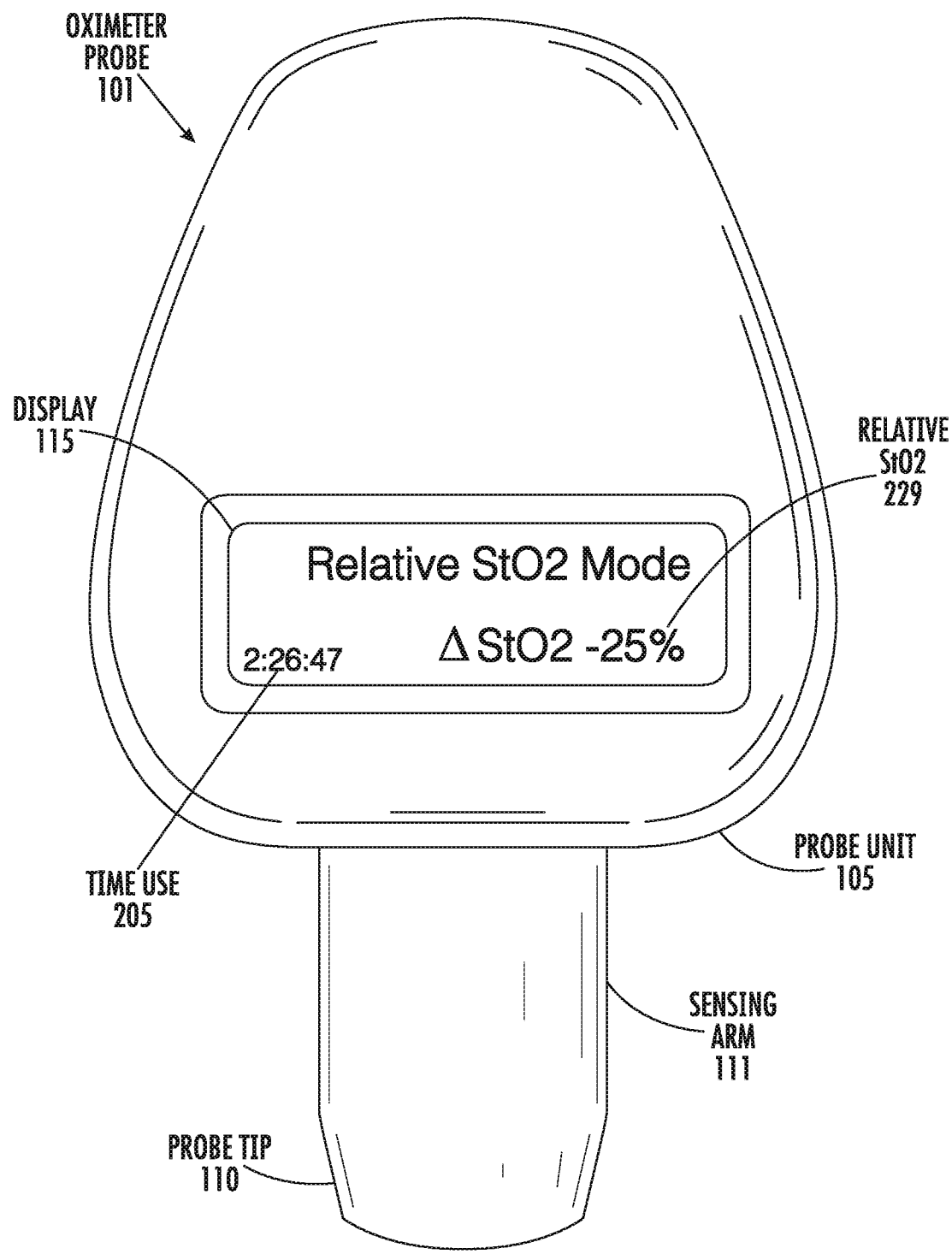
FIGS. 4C-4D show top views of the oximeter probe 101 in an implementation where the display is adapted to display a value for the relative oxygen saturation between two time points.
Figure 4D:
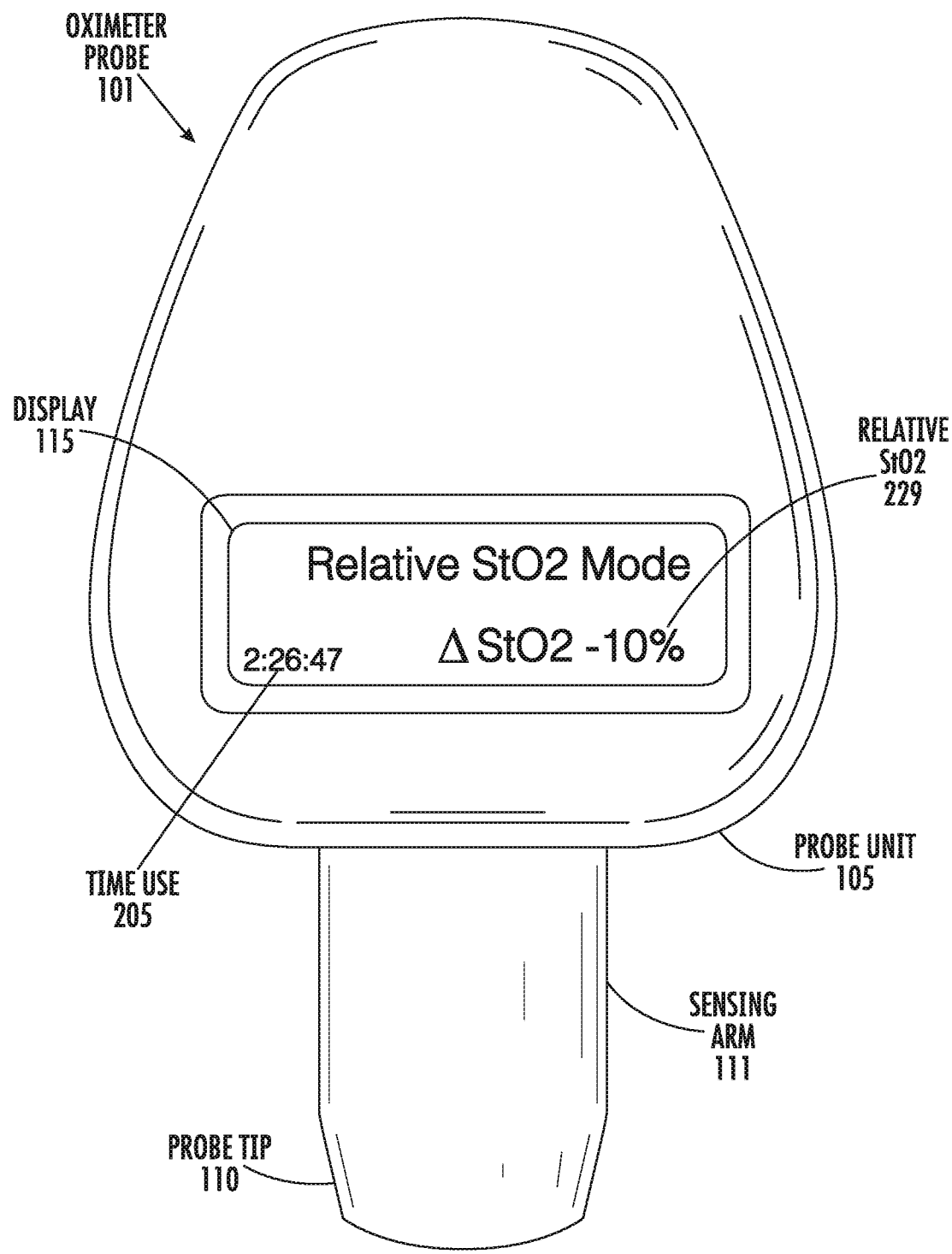

FIG. 4C shows a top view of the oximeter probe 101 in an implementation where the display is adapted to display a value for the relative oxygen saturation of tissue. The value for the relative oxygen saturation can be displayed as a percentage difference for a first value of the oxygen saturation determined for a first time and a second value of the oxygen saturation determined for a second time that is after the first time.

Figure 4E:
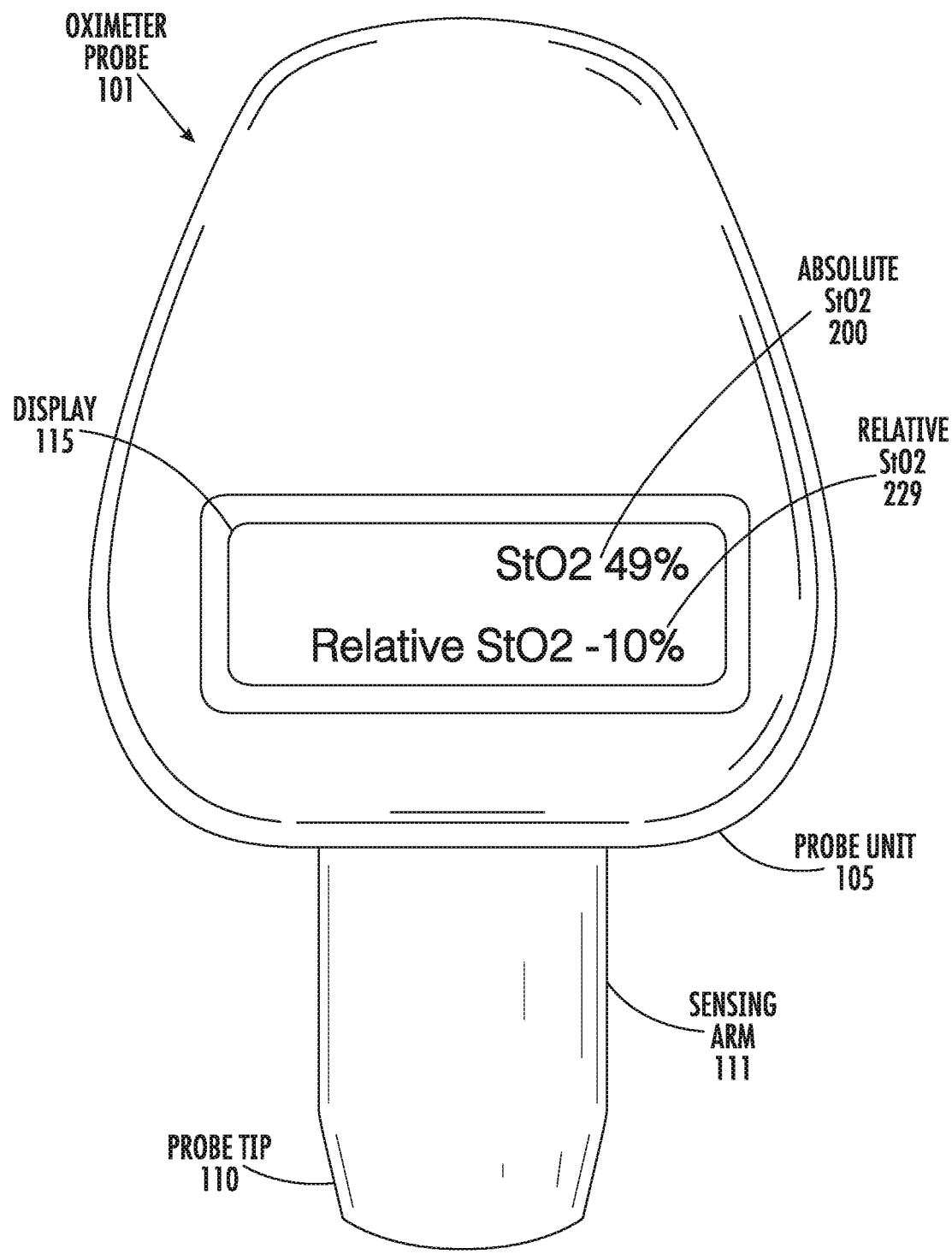
FIG. 4E shows a top view of the oximeter probe 101 where the display displays values for the absolute oxygen saturation and the relative oxygen saturation.

In an implementation, the oximeter probe can display other combinations of information, such as values for the absolute StO2 and the relative StO2, values for the total hemoglobin and the relative StO2, value for the blood volume and the relative hemoglobin. FIG. 4E shows a top view of the oximeter probe 101 where the display displays values for the absolute oxygen saturation and the relative oxygen saturation.

Figure 4F:
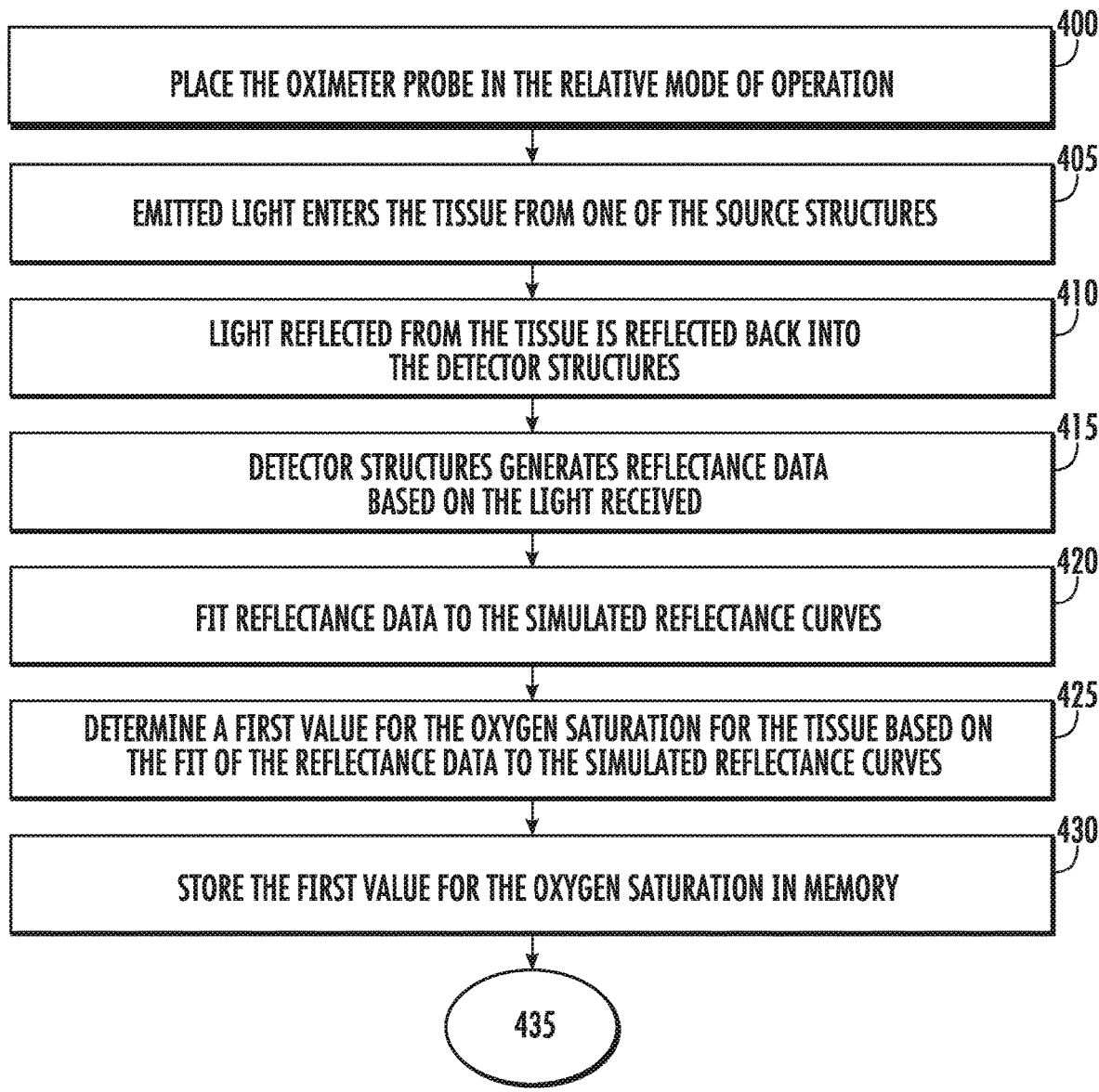
FIGS. 4F-4G show a flow diagram for a method for determining the value for the relative oxygen saturation of tissue and displaying the value on the display.
Figure 4G:
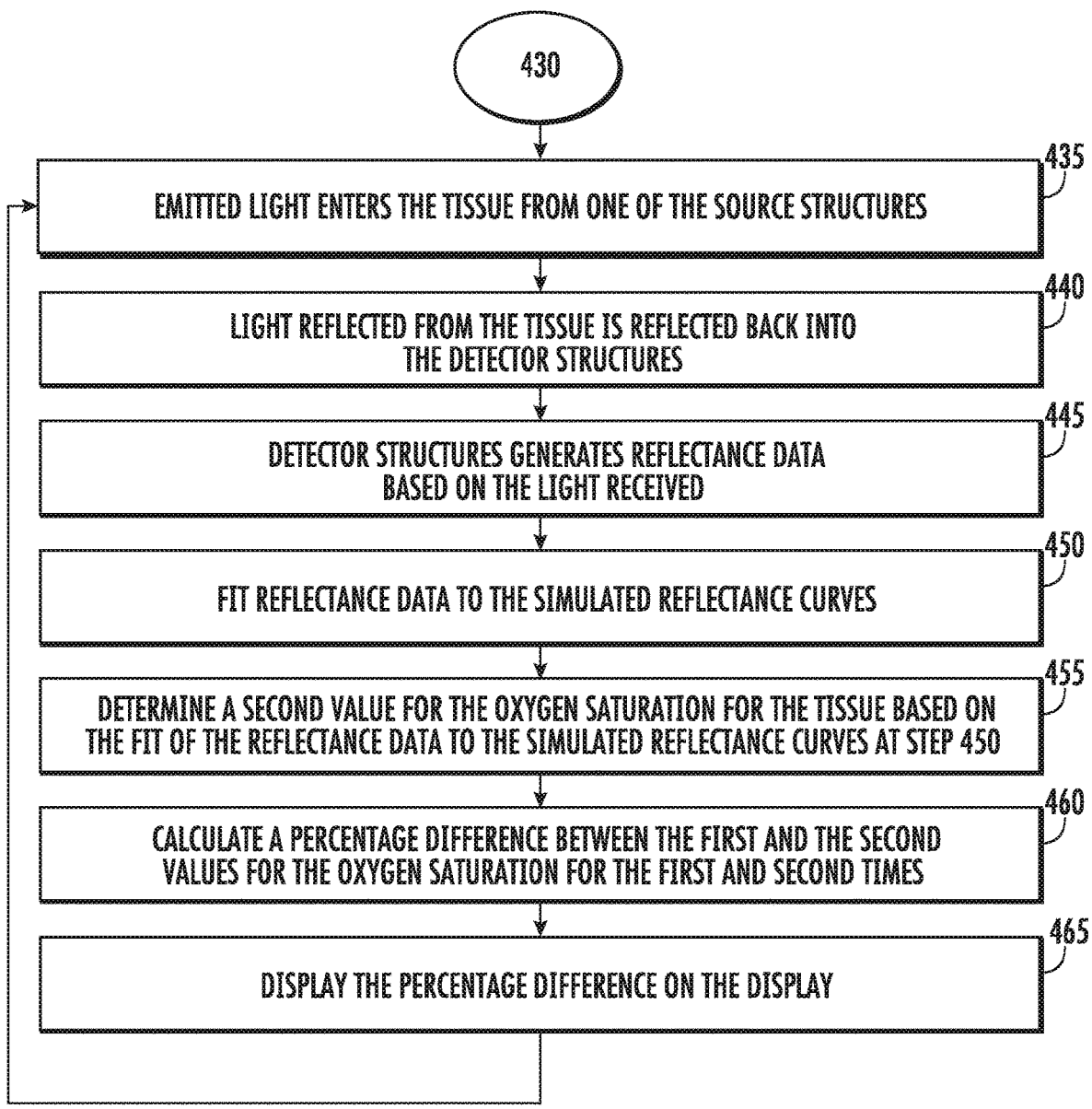

FIGS. 4F-4G show a flow diagram of a method for determining the value for the relative oxygen saturation of tissue and displaying the value on the display. The flow diagram represents one example implementation. Steps may be added to, removed from, or combined in the flow diagram without deviating from the scope of the implementation.

At 400, an input device (e.g., a button, such as button 119 or a second button, of the oximeter probe, a rocker switch of the oximeter probe, or other input device) is activated. The input device can be activated by a user. Activation of the input device places the oximeter probe into a "relative" mode of operation in which the oximeter probe can determine values for the relative oxygen saturation of tissue. The button may be activated by relatively quickly pressing the button twice (e.g., "double clicking") to place the oximeter probe in relative mode. A second activation of the input device (e.g., a subsequent double click of the button) or the activation of another input device (e.g., a third button) places the oximeter device back into an "absolute" mode in which the oximeter probe can determine values for the absolute oxygen saturation for the tissue.

At 405, oximeter probe 101 emits light (e.g., near infrared light) from one of the source structures into the tissue at a first time period. After the emitted light reflects from the tissue, detector structures 125 detect the light, step 410, and generate reflectance data for the tissue, step 415. Steps 405, 410, and 415 may be repeated for multiple wavelengths of light and for one or more other source structures, such as source structure 120b.

At 420, the oximeter probe fits the reflectance data to simulated reflectance curves 315 and determines the simulated reflectance curve to which the reflectance data has the best fit. The database that is stored in the memory and that is fit to the reflectance data can be database 900, database 1000, or database 1100, which are described below. Thereafter, the oximeter probe determines the optical properties (e.g., $\mu_a$, and $\mu_s'$ for database 900 or database 1000, or a value for melanin content, a first value for oxygen saturation, blood volume, and scattering for database 1100) for the tissue based on the optical properties of the simulated reflectance curve that best fits the reflectance data, step 425. If the oximeter probe determines $\mu_a$, and $\mu_s'$ from database 900 or 1000, for example, the oximeter probe thereafter can determine the first value for the oxygen saturation using absorption coefficient ($\mu_a$). Determination of the value for oxygen saturation from $\mu_a$ is described below.

At step 430, an input device (e.g., any of the input devices described or another input device) of the oximeter probe is activated. Activation of the input device causes the oxygen saturation value to be stored in a memory (e.g., memory 117, a buffer memory of the processor, or other memory) of the oximeter probe. A time stamp for the first value can also be stored.

At 435, oximeter probe 101 emits light (e.g., near infrared light) from one of the source structures into the tissue (can be a different tissue at a different location on the patient, such as contralateral breast tissue of two breasts or a single breast) at a second time period that is after the first time period. After the emitted light reflects from the tissue, detector structures 125 detect the light, step 440, and generate reflectance data for the tissue, step 445. Steps 435, 440, and 445 may be repeated for multiple wavelengths of light and for one or more other source structures, such as source structure 120b.

At 450, the oximeter probe fits the reflectance data to simulated reflectance curves 315 and determines the simulated reflectance curve to which the reflectance data has the best fit. The database that is stored in the memory and that is fit to the reflectance data can be database 900, database 1000, or database 1100, which are described below. Thereafter, the oximeter probe determines the optical properties (e.g., $\mu_a$, and $\mu_s'$ for database 900 or database 1000, or a second value for melanin content, a second value for oxygen saturation, a second value for the blood volume, and a second value for scattering for database 1100) for the tissue based on the optical properties of the simulated reflectance curve that best fits the reflectance data, step 455. If the oximeter probe determines second values $\mu_a$, and $\mu_s'$ from database 900 or 1000, for example, the oximeter probe thereafter can determine the second value for the oxygen saturation using absorption coefficient ($\mu_a$).

At step 460, the processor calculates a difference (e.g., a percentage difference) between the first and second values for the oxygen saturation (e.g., relative oxygen saturation). At step 465, the difference or the percentage difference for the oxygen saturation value is displayed on the display. The relative oxygen saturation value is unavailable for display until after the second time period and after the second oxygen saturation value has been determined. In an implementation, the relative oxygen saturation value is displayed symbolically on the display, indicating that the second oxygen saturation value is above (e.g., display up arrow), below (e.g., display down arrow), or equal (e.g., display a dash or other symbol) to the first oxygen saturation value. A numerical value may not be displayed for the oxygen saturation when the symbolic indicator is displayed. The symbolic indicator may be displayed when the numerical value for the oxygen saturation is displayed.

Steps 435 to 465 may be repeated in an ongoing manner for calculating subsequent values (third, fourth, fifth, and more) for the oxygen saturation, Thereby, the oximeter probe determines and displays the ongoing change in the oxygen saturation at later times relative to the value for the oxygen saturation at the first time. Entry and exit from the relative mode can reset the first value for the oxygen saturation.

The steps of the method shown in FIG. 4F-4G can be repeated for a number of tissue measurements, such as a first tissue measurement at a first time, a second tissue measurement at a second time (after the first time period), a third tissue measurement at a third time (after the second time period), or more tissue measurements at later times. Calculated and displayed relative oxygen saturation values can be for the first and second tissue measurements (e.g., first relative oxygen saturation), the second and third tissue measurements (e.g., second relative oxygen saturation), or the first and third tissue measurements (e.g., third relative oxygen saturation). The first, second, and third tissue measurements can be for the same tissue location, two different tissue locations, or three different tissue locations. The display of the first, second, or third relative oxygen saturation values (e.g., first, second, and third modes of operation) can be selected by a user via operation of a user input (e.g., button 119, touch screen, or others).

Two or more of the three modes of operation can be operation simultaneously so that the first and second relative oxygen saturation values are display at the same time (e.g., without the third relative oxygen saturation value being displayed), the second and third relative oxygen saturation values are display at the same time (e.g., without the first relative oxygen saturation value being displayed), and the first and third relative oxygen saturation values are display (e.g., without the second relative oxygen saturation value being displayed) at the same time.

In an implementation, the oximeter probe is adapted to provide a notification if percentage difference for the oxygen saturation value (e.g., the relative oxygen saturation values) is greater or less than a threshold amount or if the absolute value for the oxygen saturation is greater or less than the threshold amount. The threshold amount can be an amount entered into the oximeter probe by a user, selected from a displayed amount displayed on the display, or wire or wirelessly entered in the oximeter probe. The amount can be the value entered at step 470 of FIG. 4J. If the percentage difference is above or below the threshold value, the displayed oxygen saturation value may be displayed with one or more additional indicators, such as an up arrow, a down arrow, flashing display, colored displayed value (e.g., red or green), a lighted red LED, a lighted green LED, a lighted red set of pixels on the display (e.g., red or green), or other indicator. The oximeter probe may emit one or more sounds (e.g., tones or clicks) or may provide haptic feedback (e.g., vibrations) if the percentage value for the oxygen saturation is above or below the threshold. In some implementations, one or more of these additional notifications are displayed if the percentage difference is below the threshold value (e.g., oxygen saturation dropping), but not above the threshold value (e.g., oxygen saturation increasing).

The oximeter probe can be adapted to display the percentage difference for the oxygen saturation value if the percentage difference for the oxygen saturation (e.g., relatively oxygen saturation) or if the absolute value for the oxygen saturation is greater or less than the threshold amount is above or below the threshold value by an absolute amount (e.g., threshold plus an offset value, and threshold minus the offset value). The offsets above and below the threshold value can be equal or unequal, such as: the threshold value plus 2 percent of the threshold value and the threshold value minus 2 percent of the threshold value; the threshold value plus 5 percent of the threshold value and the threshold value minus 5 percent of the threshold value; the threshold value plus 1 percent of the threshold value and the threshold value minus 5 percent of the threshold value; the threshold value plus 5 percent of the threshold value and the threshold value minus 2 percent of the threshold value; or other values. The upper and lower absolute percentages above and below the threshold value can be entered into the oximeter probe by a user, selected from a displayed amount displayed on the display, or wire or wirelessly entered in the oximeter probe. If the percentage difference is above or below the threshold value plus or minus the absolute offsets, the displayed oxygen saturation value may be displayed with one or more additional indicators, such as an up arrow, a down arrow, flashing display, colored displayed value (e.g., red or green), a lighted red LED, a lighted green LED, a lighted red set of pixels on the display (e.g., red or green), or other indicator. The oximeter probe may emit one or more sounds (e.g., tones or clicks) or may provide haptic feedback (e.g., vibrations) if the percentage value for the oxygen saturation is above or below the threshold. In some implementations, one or more of these additional notifications are displayed if the percentage difference is below the threshold value (e.g., oxygen saturation dropping), but not above the threshold value (e.g., oxygen saturation increasing). In some implementations, one or more of these additional notifications are displayed if the percentage difference is below the threshold value (e.g., oxygen saturation dropping), but not above the threshold value (e.g., oxygen saturation increasing).

Figure 4H:
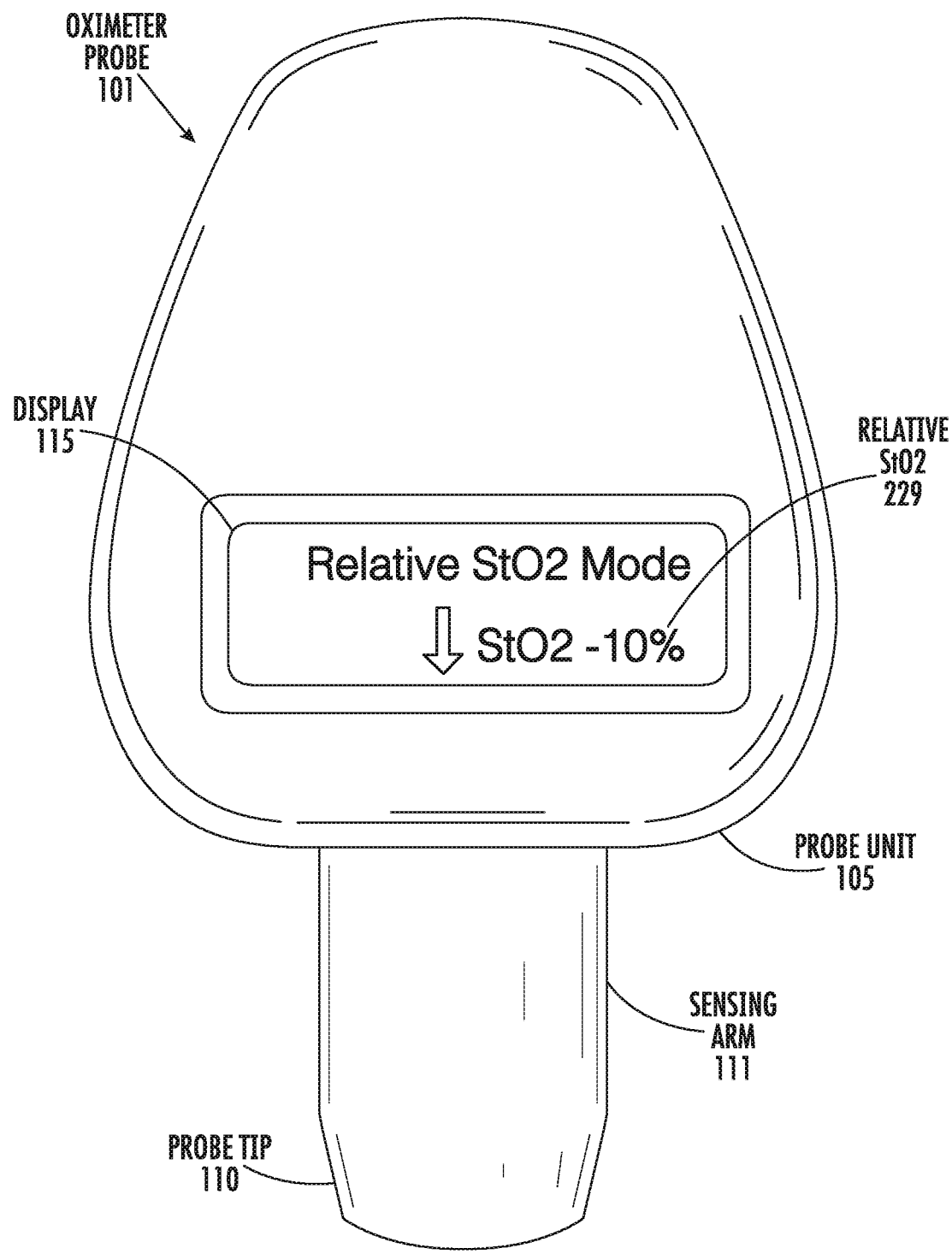
FIGS. 4H-4I show top views of the oximeter probe 101 where the display displays values for the relative oxygen saturation and arrows to further indicate increases and decreases in the relative oxygen saturation.
Figure 4I:
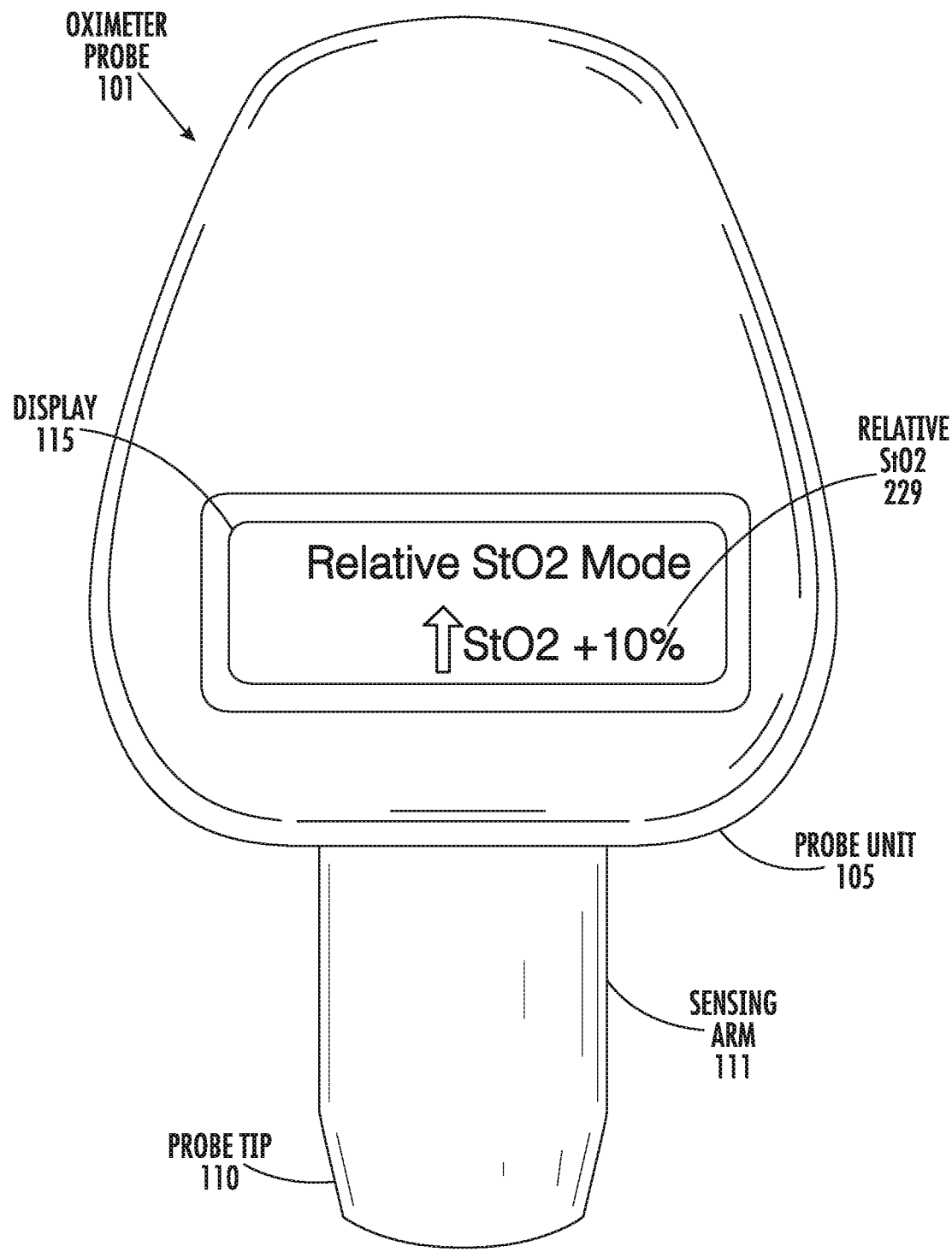

In an implementation, the oximeter probe is adapted to display the difference between the first and second values for the oxygen saturation rather than the percentage difference between the first and second values for the oxygen saturation. The oximeter probe can display the percentage difference or the calculated difference with one or more of a variety of indicators that indicate the relative oxygen saturation has increased or decreased. For example, a decreased value of the relative oxygen saturation can be displayed with a down arrow (FIG. 4H), with a colored indicator (e.g., red dot on the display or a lighted red lighting element, such as a red LED in the probe unit 105). For example, an increased value of the relative oxygen saturation can be displayed with an up arrow (FIG. 4I), with a colored indicator (e.g., green dot on the display or a lighted green lighting element, such as a green LED in the probe unit 105). The value for the relative oxygen saturation can be displayed in a first color (e.g., red) if the value decreases and a second color (e.g., green) if the value increases. The oximeter probe can display the value for the percentage difference or the calculated difference as flashing, for example, if the values decrease. The oximeter probe can be adapted to emit one or more noises, for example, if these values decrease. The oximeter probe can be adapted to provide haptic feedback (e.g., a vibration) if these values decrease. Each of these additional indicators (e.g., arrows, emitted light, flashing display, values displayed with colors, sound, haptic feedback, or other indicators) can be emitted if the relative oxygen saturation decreases below the lower threshold value, increases above the upper threshold value, or both.

The relative mode of operation can be useful for a number of medical procedures where knowledge of the relative changes in value for the oxygen saturation (relative oxygen saturation value) are helpful for determining whether a medical procedure can be started, proceed, or should be stopped. For example, when a reduced blood flow is desired in tissue, an epinephrine injection or other medication may be administered to the patient (e.g., may be locally administered to tissue) to reduce blood flow in the tissue. A baseline value for the hemoglobin content or blood volume of the tissue can be determined (e.g., at steps 405-425, determining a first value of hemoglobin content or blood volume, for example using database 1100 described below) prior to administering the epinephrine or a relatively short time after the medication is administered.

Thereafter, based on the ongoing display of the updated relative hemoglobin or blood volume values (e.g., at steps 435-425, determining a second value of hemoglobin content or blood volume, for example using database 1100), a practitioner can determine whether the epinephrine administration has been successful is reducing blood flow, whether more epinephrine needs to be administered to the patient to further reduce the blood flow in the tissue, or whether a procedure should be stopped. That is, as the oximeter probe displays the updated relative hemoglobin or blood volume values, the practitioner can "observe" the medication taking effect on the tissue.

Figure 4J:
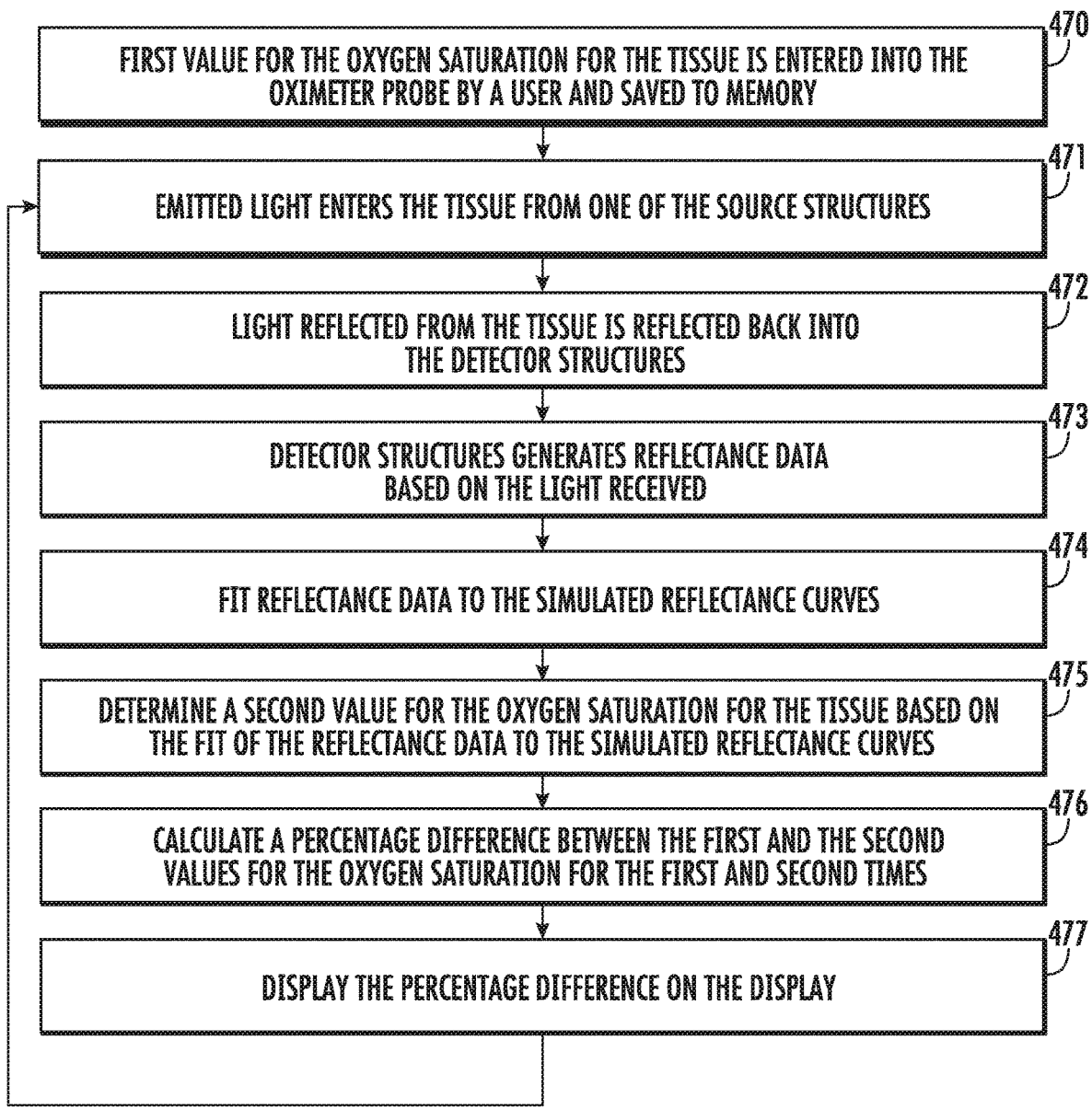
FIG. 4J shows a flow diagram of a method for determining the value for the relative oxygen saturation of tissue where the use enters or selects the first value for the oxygen saturation and the probe determines the latter second value for the oxygen saturation.

FIG. 4J shows a flow diagram of a method for determining the value for the relative oxygen saturation of tissue and displaying the value on the display. The flow diagram represents one example implementation. Steps may be added to, removed from, or combined in the flow diagram without deviating from the scope of the implementation.

At 470 the oximeter prove receives that first value for the oxygen saturation via an input, such as a user input or an input from another device. The user input may be entered via one or more button presses of the button or other input device, such as a touch screen. The first value of the oxygen saturation may also be input in the oximeter probe via a wired or wireless connection with the probe. In some implementations, the oximeter probe may display a range of first values for the oxygen saturation that a user can choose from, for example, by a button press or other input.

At 471, oximeter probe 101 emits light (e.g., near infrared light) from one of the source structures into the tissue. After the emitted light reflects from the tissue, detector structures 125 detect the light, step 472, and generate reflectance data for the tissue, step 473. Steps 471, 472, and 473 may be repeated for multiple wavelengths of light and for one or more other source structures, such as source structure 120b.

At 474, the oximeter probe fits the reflectance data to simulated reflectance curves 315 and determines the simulated reflectance curve to which the reflectance data has the best fit. The database that is stored in the memory and that is fit to the reflectance data can be database 900, database 1000, or database 1100, which are described below. Thereafter, the oximeter probe determines the optical properties (e.g., $\mu_a$, and $\mu_s'$ for database 900 or database 1000, or a second value for melanin content, a second value for oxygen saturation, a second value for the blood volume, and a second value for scattering for database 1100) for the tissue based on the optical properties of the simulated reflectance curve that best fits the reflectance data, step 475. If the oximeter probe determines second values $\mu_a$, and $\mu_s'$ from database 900 or 1000, for example, the oximeter probe thereafter can determine the second value for the oxygen saturation using absorption coefficient ($\mu_a$).

At step 476, the processor calculates a difference (e.g., a percentage difference) between the first and second values for the oxygen saturation. At step 477, the percentage difference for the oxygen saturation value is displayed on the display.

Steps 471 to 477 may be repeated in an ongoing manner for calculating subsequent values (third, fourth, fifth, and more) for the oxygen saturation, Thereby, the oximeter probe determines and displays the ongoing change in the oxygen saturation at later times relative to the value for the oxygen saturation at the first time. Entry and exit from the relative mode can reset the first value for the oxygen saturation.

Figure 4K:
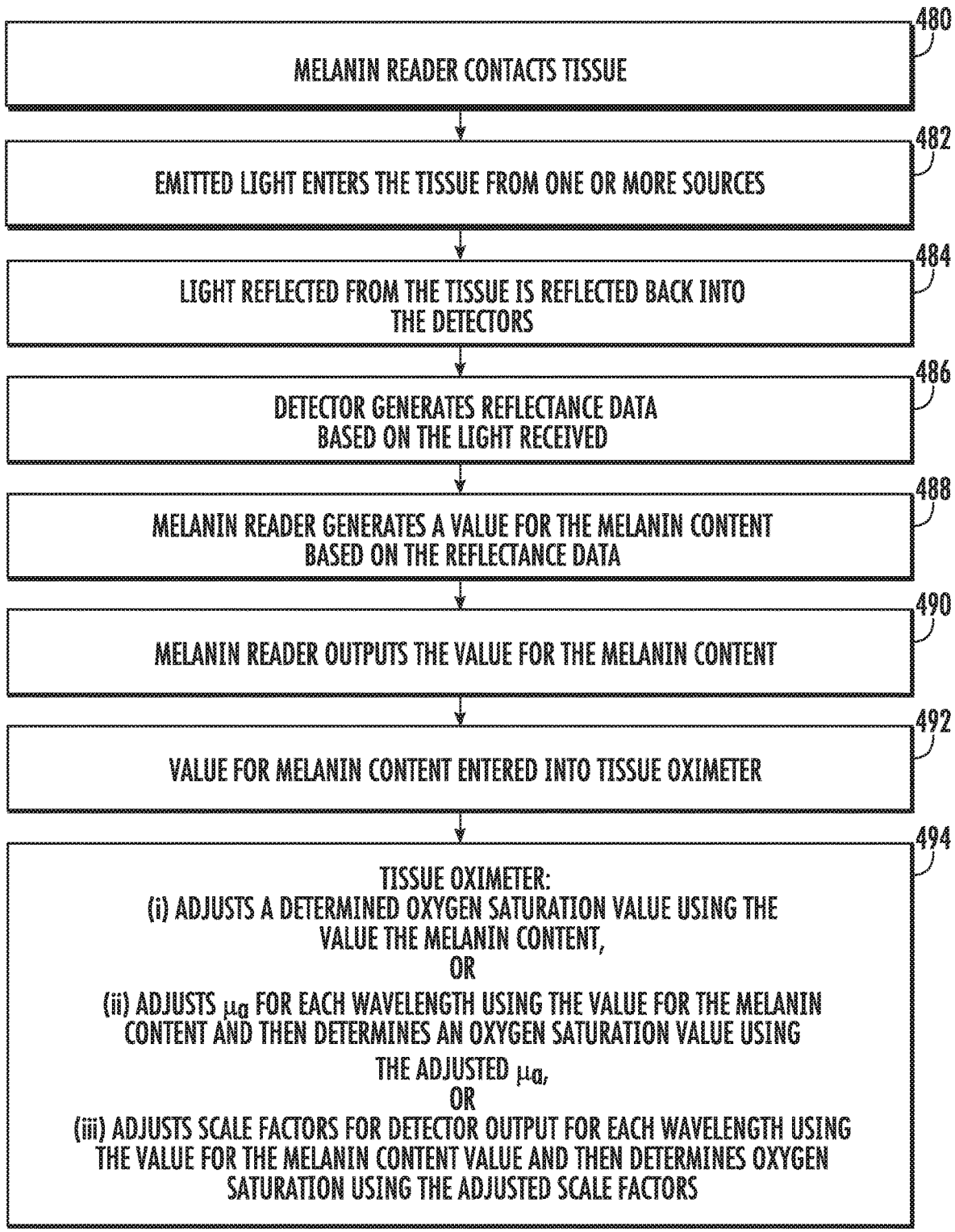
FIG. 4K shows a flow diagram of a method for determining optical properties of tissue (e.g., real tissue) by the oximeter probe in an implementation.

Tissue Analysis. FIG. 4K shows a flow diagram of a method for determining optical properties of tissue (e.g., real tissue) by oximeter probe 101 in an implementation. The oximeter probe uses determined melanin content for the tissue to correct various tissue parameters that are measured by the oximeter probe. The flow diagram represents one example implementation. Steps may be added to, removed from, or combined in the flow diagram without deviating from the scope of the implementation.

At 480, a melanin reader optically couples (e.g., contacts) to the tissue. Melanin readers are optoelectronic devices that are adapted for emitting light, step 482, into tissue, and detecting the light, step 484, after having been transmitted through the tissue or reflected from the tissue. The light detected by the melanin reader is converted to electrical signals, step 486, that are used by the device to determine melanin content of the tissue, step 488. The melanin reader can output a value for the melanin content, step 490, on a display of the reader or via a wired or wireless output.

In an implementation, at 492, information (e.g., a numerical value) about the melanin content is entered into oximeter probe 101. The information can be entered into the oximeter probe via a user (e.g., a human user) or via a wired or wireless communication between the melanin reader and the oximeter probe.

In a first implementation, at 494, the oximeter probe uses the information for the melanin content to adjust one or more measured values generated by the probe. In an implementation, the oximeter probe determines a value for the oxygen saturation of the tissue. The oximeter probe thereafter adjusts the value for the oxygen saturation using the information for the melanin content. The oximeter probe can adjust the value for the oxygen saturation via one or more arithmetic operations, mathematical functions, or both. For example, the information for the melanin content can be used as an offset (e.g., additive offset), a scale factor, or both for adjusting the value for the oxygen saturation.

In an alternative implementation, at 494, the oximeter probe determines the absorption coefficient $\mu_a$ (mua), the reduced scattering coefficient $\mu_s'$ (mus prime), or both for the tissue for a number of wavelengths of light (e.g., four wavelengths of light) emitted and detected by the oximeter probe. Thereafter, the oximeter probe adjusts the determined absorption ($\mu_a$) values for each wavelength of light using the information about melanin content. The oximeter probe can adjust the absorption coefficient ($\mu_a$) values via one or more arithmetic operations, mathematical functions, or both. For example, the information for the melanin content can be used as an offset (e.g., additive offset), a scale factor, or both for adjusting the absorption ($\mu_a$) values. Thereafter, the oximeter probe uses the absorption ($\mu_a$) values to determine a value for the oxygen saturation for the tissue. Determination of absorption ($\mu_a$) and reduced scattering ($\mu_s'$) are described below.

In another implementation, at 494, the oximeter probe applies one or more melanin correction functions to reflectance data generated by the detector structures. The melanin correction functions are based on the information for the melanin content. The reflectance data can be analog reflectance data generated by the detector structures prior to being digitized by one or more electronic components of the oximeter probe or the reflectance data can be digitized reflectance data. The melanin correction functions can be applied to the analog reflectance data or the digitized reflectance data. The melanin correction function includes one or more mathematical operations that are applied to the reflectance data. The scale factors are determined by the oximeter probe based on information for the melanin content that is entered into the oximeter probe. The reflectance data can be adjusted for melanin content for each wavelength of light emitted by the oximeter probe.

In an implementation, the melanin correction function can be a combined function (e.g., having scale factors) that is combined with one or more calibration functions (e.g., having scale factors). The calibration function can include scale factors for correcting the detector responses based on a variety of factors, such as differences that occur as a result of manufacturing, that occur as a result of temperature drift of the detector structures, or other considerations. After the reflectance data are adjusted by the oximeter probe, the probe can then determine the oxygen saturation of blood in the tissue to be measured.

Figure 5:
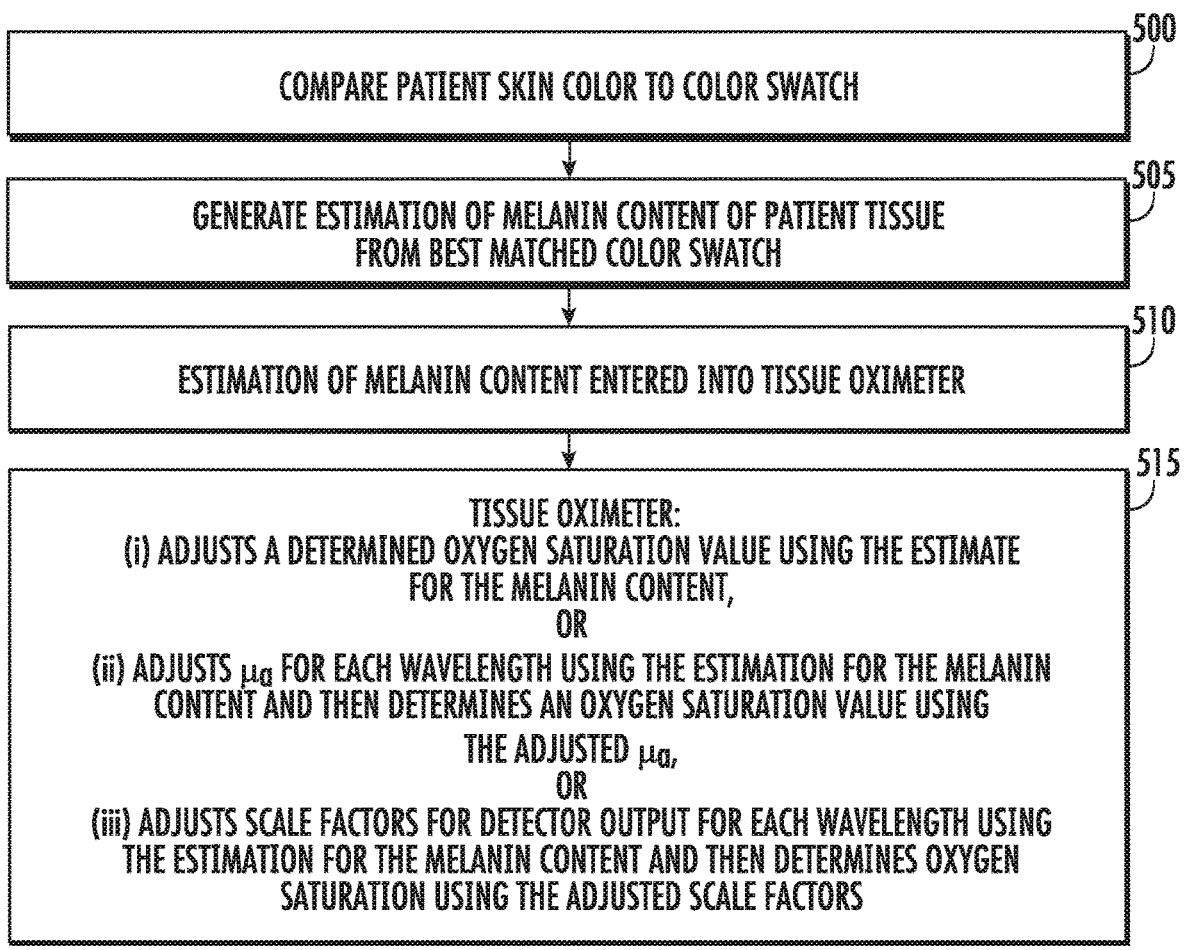
FIG. 5 shows a flow diagram of a method for determining optical properties of tissue by the oximeter probe in an implementation.

FIG. 5 shows a flow diagram of a method for determining optical properties of tissue by oximeter probe 101 in an implementation. The oximeter probe uses information about the melanin content for the tissue to correct various tissue parameters measured by the oximeter probe. The flow diagram represents one example implementation. Steps may be added to, removed from, or combined in the flow diagram without deviating from the scope of the implementation.

At 500, the color of the tissue is compared to two or more color samples of a number of color samples (sometimes referred to as color swatches) to determine whether the color of one of the color samples approximately matches the color of the tissue. Each color sample used for the color comparison is associated with a value of melanin content. Information (e.g., a numerical value) that identifies the melanin content for the color sample can be located on the color sample.

The comparison between the color of the tissue and the color of the color samples can be performed by a color comparison tool, such as one or more of the color comparison tools of X-Rite, Incorporated of Grand Rapids Mich. In an implementation, the comparison can be performed visually by a human, such as the patient or a medical provider. In an implementation, the oximeter probe is adapted to determine a value for the melanin content of the tissue, which can displayed on the display of the probe. An implementation of the oximeter probe is adapted to emit one or more wavelength of light, such as visible light or IR, for determining the melanin content of the tissue.

At 505, subsequent to the comparison, the value for the melanin content of the tissue is determined based on the comparison.

In an alternative implementation, the value for the melanin content is determined from an estimate of the content based on a finite range of melanin content values. The number of values in a range for melanin content can include two or more values. For example, the number of values in a range for melanin contents can be 2 (e.g., 1 for light tissue and 2 for dark tissue), 3 (e.g., 1 for light, 2 for medium, and 3 dark), 4, 5, 6, 7, 8, 9, 10 or more. An estimation of the value for melanin content can be provided by the patient or a medical provider.

At 510, the information about the melanin content can be entered into the oximeter probe. Step 510 can be skipped in a method where the oximeter probe determines the value for the melanin content. Button 119 can be activated a predetermined number of times to place the oximeter probe into a data entry mode in which the information for the melanin content can be entered. The information for the melanin content can thereafter be entered into the probe by further activation of the button, via a wired communication with the probe, via a wireless communication with the probe, via the display if the display is a touch interface display, via an audible interface (e.g., a microphone and voice recognition software in the probe), or by other input techniques.

At 515, the oximeter probe is adapted to use information about the melanin content to adjust one or more measurements or calculations performed by the oximeter probe. For example, the oximeter probe can use the information to adjust oxygen saturation value for the tissue, adjust absorption ($\mu_a$), adjust reduced scattering ($\mu_s'$), adjust values generated by the detector(s), or one or more of a combination of these adjustments. Each of these adjustments is described further above with respect to step 435.

Figure 6:
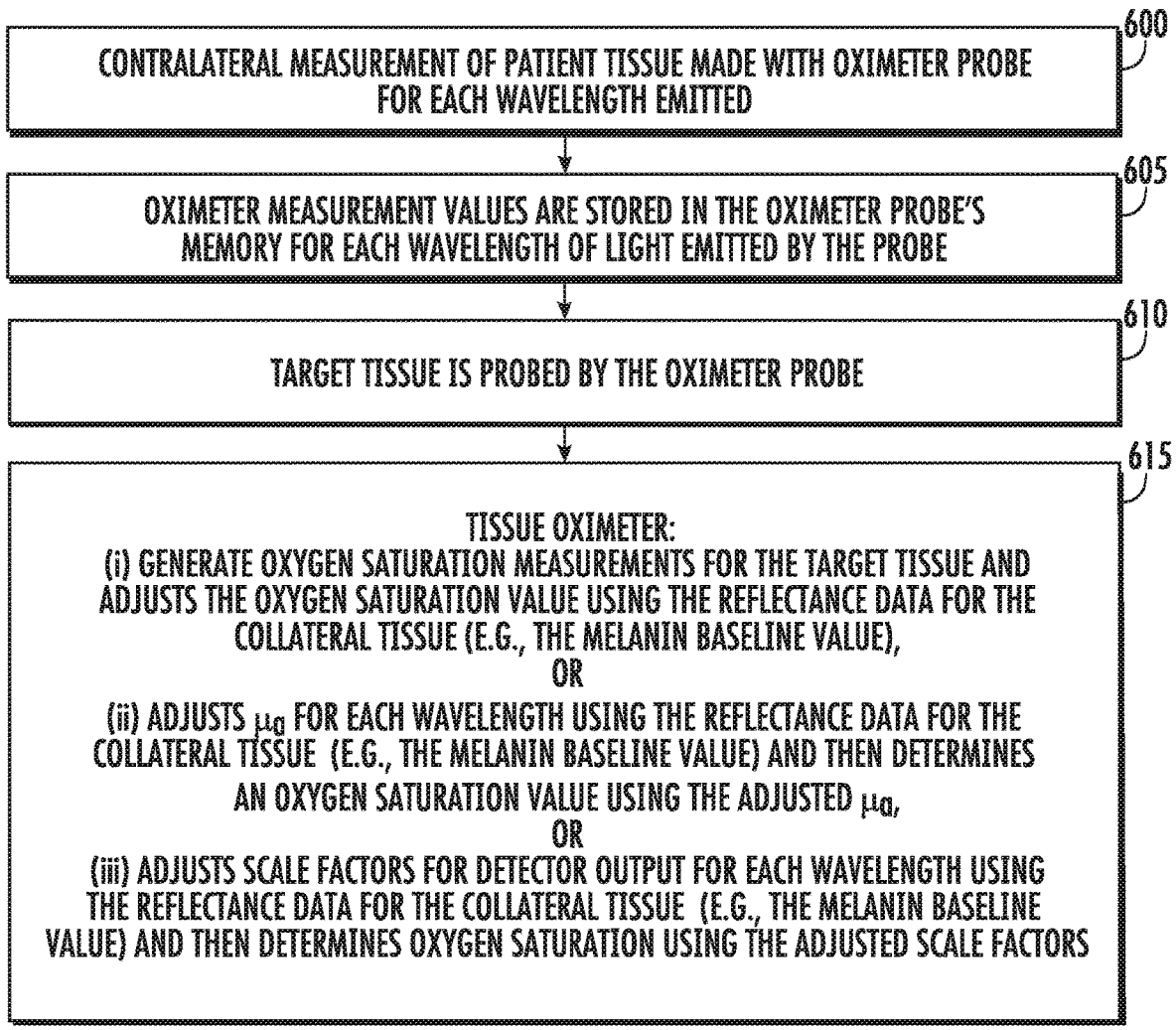
FIG. 6 shows a flow diagram of a method for determining optical properties of tissue by the oximeter probe in an implementation.

FIG. 6 shows a flow diagram of a method for determining optical properties of tissue by oximeter probe 101 in an implementation. The oximeter probe uses the determined melanin content of the tissue to correct various tissue parameters that are measured by the probe. The flow diagram represents one example implementation. Steps may be added to, removed from, or combined in the flow diagram without deviating from the scope of the implementation.

At 600, one or more contralateral measurements of the tissue are made with the oximeter probe. The contralateral measurements are made using the oximeter probe on a portion of healthy tissue (e.g., healthy breast tissue) before a measurement is made using the oximeter probe on target tissue that is to be measured (e.g., breast tissue for which tissue health is to be determined). The contralateral measurements of the tissue can be made for each wavelength of light emitted by the oximeter probe.

At 605, reflectance data generated by the detector structures are digitized by the electronic elements of the oximeter probe and are stored in memory. The reflectance data provide a basis of comparison for subsequent tissue measurement. For example, the contralateral measurements provide baseline measurements of the melanin content of the contralateral tissue where the baseline measurements can be used by the processor to correct for various measurements made the oximeter probe.

At 610, oximetry measurements of the target tissue to be measured are made by the oximeter probe.

At 615, in an implementation, the processor generates oxygen saturation values for target tissue using the oximetry measurements. Thereafter, the processor retrieves the stored reflectance data stored at 605 for the contralateral tissue and uses the retrieved values to adjust the oxygen saturation values. That is, the processor uses the baseline measurement for melanin content for the healthy contralateral tissues tissue to adjust the oxygen saturation values of the target tissue.

At 615, in an alternative implementation, the processor determines absorption $\mu_a$, reduced scattering coefficient $\mu_s'$, or both from the oximetry measurements of the target tissue. Thereafter, the processor retrieves the reflectance data stored at 605 for the contralateral tissue and uses the retrieved values to adjust $\mu_a$, $\mu_s'$, or both. The processor then uses the adjusted $\mu_a$ value to calculate values for oxygenated hemoglobin, deoxygenated hemoglobin, or other values for the target tissue. That is, the processor uses the baseline measurement for melanin content of the healthy contralateral tissue to adjust $\mu_a$ for the target tissue.

At 615, in an another alternative implementation, the processor retrieves the stored reflectance data stored at 605 for the contralateral tissue and uses the retrieved values to adjust the reflectance data generated by the detector structures for the target tissue. The adjustments applied by the processor to the reflectance data can be simple offsets (e.g., addition offsets), scale factors (e.g., multiplication offsets), functional corrections, other corrections, or any one or these adjustments in any combination. That is, the processor adjusts the values generated by the detector structures using the baseline measurement for melanin content for the healthy tissue to adjust the reflectance data for the target tissue.

Stored Simulated Reflectance Curves. According to an implementation, memory 117 stores a number of Monte-Carlo-simulated reflectance curves 315 ("simulated reflectance curves"), which may be generated by a computer for subsequent storage in the memory. Each of the simulated reflectance curves 315 represents a simulation of light (e.g., near infrared light) emitted from one or more simulated source structures into simulated tissue and reflected from the simulated tissue into one or more simulated detector structures. Simulated reflectance curves 315 are for a specific configuration of simulated source structures and simulated detector structures, such as the configuration of source structures 120a-120b and detector structures 125a-125h of probe tip 110 having the source-to-detector spacing described above with respect to FIG. 2.

Therefore, simulated reflectance curves 315 model light emitted from the source structures and collected by the detector structures of oximeter probe 101. Further, each of the simulated reflectance curves 315 represents a unique real tissue condition, such as specific tissue absorption and tissue scattering values that relate to particular concentrations of tissue chromophores and particular concentrations of tissue scatterers. For example, the simulated reflectance curves can be generated for simulated tissue having various melanin contents, various oxygenated hemoglobin concentrations, various deoxygenated hemoglobin concentrations, various concentrations of water, a static value for the concentrations of water, various concentration of fat, a static value for the concentration of fat, or various absorption ($\mu_a$) and reduced scattering ($\mu_s'$) values.

The number of simulated reflectance curves stored in memory 117 may be relatively large and can represent nearly all, if not all, practical combinations of optical properties and tissue properties that may be present in real tissue that is analyzed for viability by oximeter probe 101. While memory 117 is described as storing Monte-Carlo-simulated reflectance curves, memory 117 may store simulated reflectance curves generated by methods other than Monte-Carlo methods, such as using a diffusion approximation.

Figure 7:
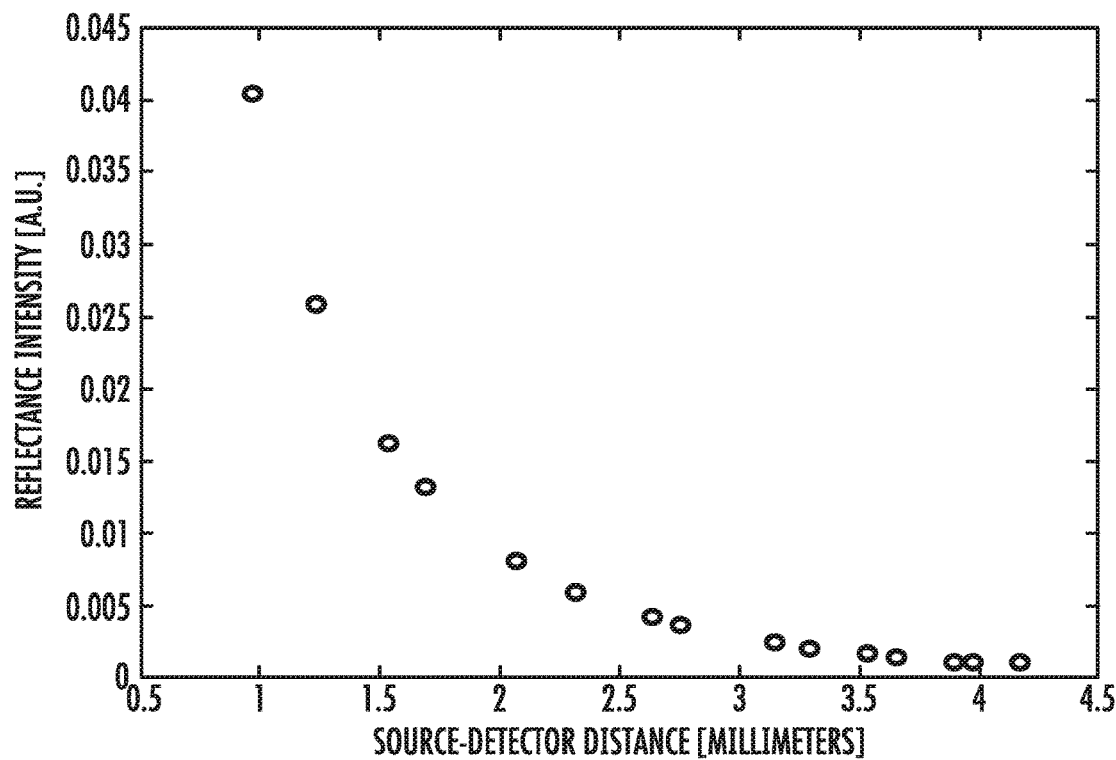
FIG. 7 shows an example graph of a reflectance curve, which may be for a specific configuration of source structures and detector structures, such as the configuration source structures and detector structures of the probe tip.

FIG. 7 shows an example graph of a reflectance curve, which may be for a specific configuration of source structures 120 and detector structures 125, such as the configuration source structures and detector structures of probe tip 110. The horizontal axis of the graph represents the distances between source structures 120 and detector structures 125 (i.e., source-to-detector distances). If the distances between source structures 120 and detector structures 125 are appropriately chosen, and the simulated reflectance curve is a simulation for source structures 120 and detector structures 125, then the lateral spacings between the data points in the simulated reflectance curve will be relatively uniform. Such uniform spacings can be seen in the simulated reflectance curve in FIG. 7. The vertical axis of the graph represents the simulated reflectance of light that reflects from tissue and is detected by detector structures 125. As shown by the simulated reflectance curve, the reflected light that reaches detector structures 125 varies with the distance between source structures and detectors structures, with the reflected light detected at smaller source-to-detectors distances greater than the reflected light detected a larger source-to-detector distances.

Figure 8:
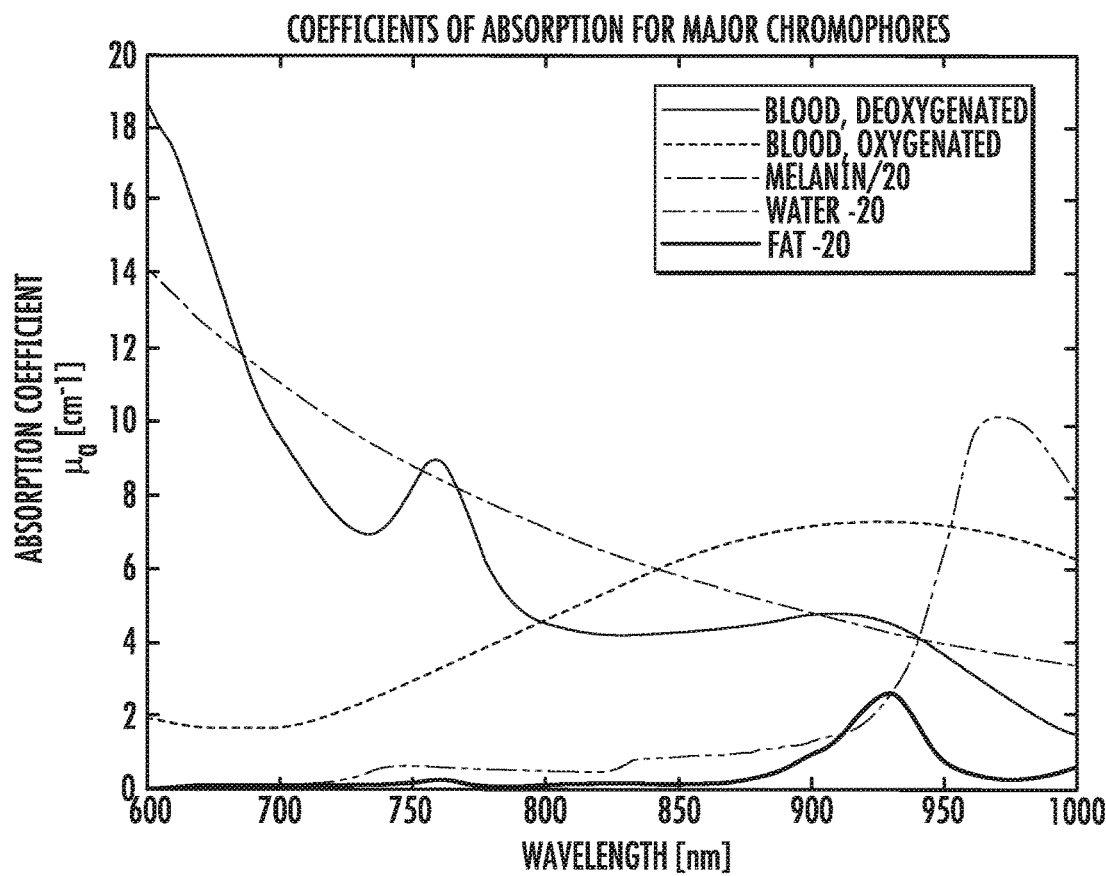
FIG. 8 shows a graph of the absorption coefficient $\mu_a$ in arbitrary units versus wavelength of light for oxygenated hemoglobins, deoxygenated hemoglobins, melanin, and water in tissue.

FIG. 8 shows a graph of the absorption coefficient $\mu_a$ versus wavelength of light for some significant tissue chromophores: blood containing oxygenated hemoglobin, blood containing deoxygenated hemoglobin, melanin, and water. In an implementation, the Monte-Carlo simulations used for generating the simulated reflectance curve are functions of one or more select chromophores that may be present in tissue. The chromophores can include melanin, oxygenated hemoglobin, deoxygenated hemoglobin, water, lipid, cytochrome, or other chromophores, in any combination. Oxygenated hemoglobins, deoxygenated hemoglobins, and melanin are the most dominant chromophores in tissue for much of the visible and near-infrared spectral range.

In an implementation, memory 117 stores a select number of data points for each of the simulated reflectance curves 315 and might not store the entirety of the simulated reflectance curves. The number of data points stored for each of the simulated reflectance curves 315 may match the number of source-detector pairs. For example, if probe tip 110 includes two source structures 120a-120b and includes eight detector structures 125a-125h, then oximeter probe 101 includes sixteen source-detector pairs, and memory 117 may thus store sixteen select data points for each of the simulated reflectance curves for each wavelength of light emitted by source structure 120a or source structure 120b. In an implementation, the stored data points are for the specific source-to-detectors distances of probe tip 110, such as those shown in table 1.

Thus, the simulated reflectance curve database stored in memory 117 might be sized 16×5850 where sixteen points are stored per curve that may be generated and emitted by each source structure 120 and measured by each detector structure 125, where there are a total of 5850 curves spanning the optical property ranges. Alternatively, the simulated reflectance curve database stored in memory 117 might be sized 16×4×5850 where sixteen points are stored per curve for four different wavelengths that may be generated and emitted by each source structure and where there are a total of 5850 curves spanning the optical property ranges. The 5850 curves originate, for example, from a matrix of 39 scattering coefficients $\mu_s'$ values and 150 absorption coefficient $\mu_a$ values. In other implementations, more or fewer simulated reflectance curves are stored in the memory. For example, the number of simulated reflectance curves stored in memory can range from about 100 curves, to about 250,000 curves, to about 400,000 curves, or more.

The reduced scattering coefficient $\mu_s'$ values might range from 5:5:24 per centimeter. The $\mu_a$ values might range from 0.01:0.01:1.5 per centimeter. It will be understood that the foregoing described ranges are example ranges and the number source-detectors pairs, the number of wavelengths generated and emitted by each source structure, and the number of simulated reflectance curves may be smaller or larger.

Figures 9, 10:
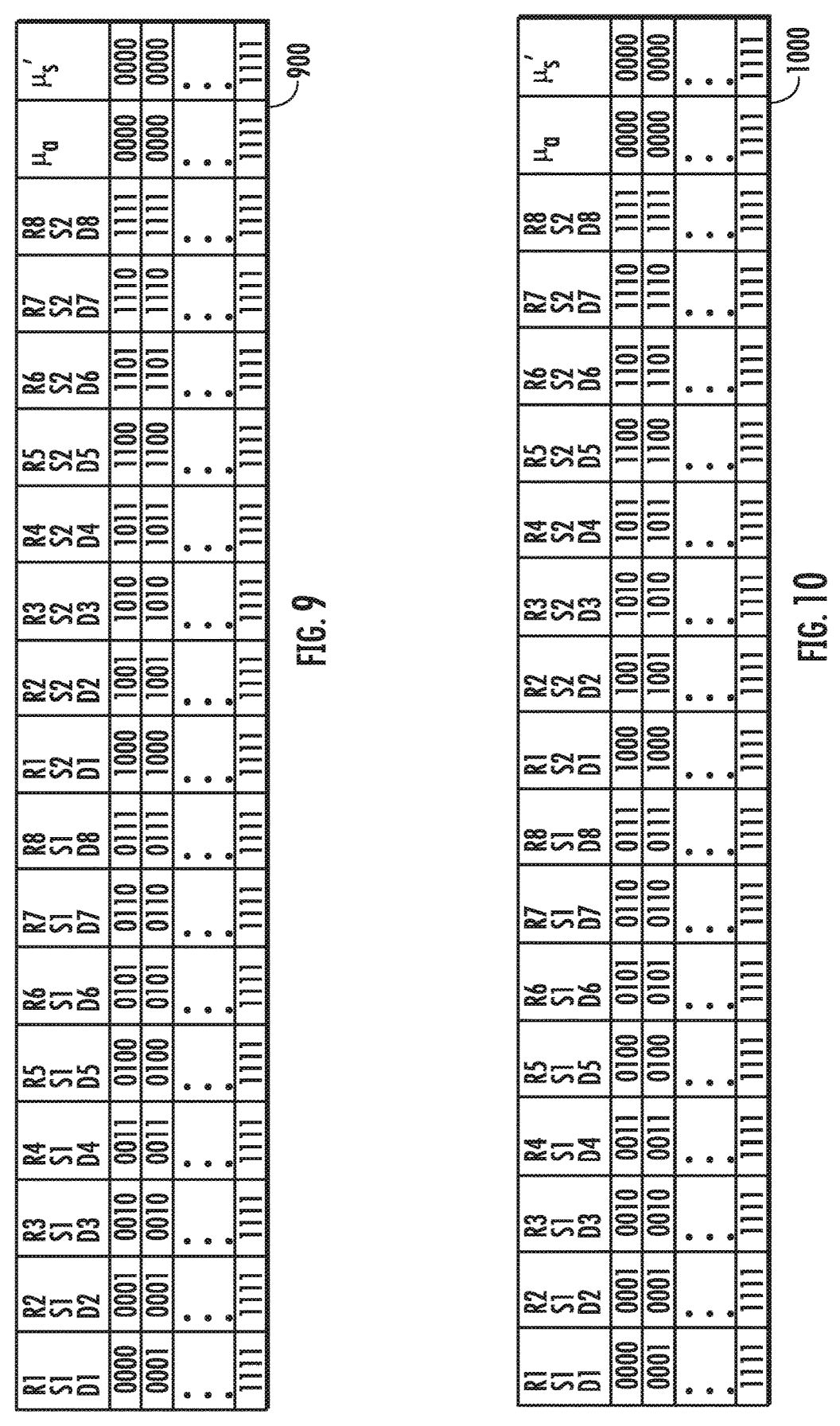

FIG. 9 shows a database 900 of simulated reflectance curves 315 that is stored in the memory of the oximeter probe in an implementation. The database is for a homogeneous model of tissue. Each row in the database represents one simulated reflectance curve generated from a Monte-Carlo simulation for simulated light emitted into simulated tissue from two simulated source structures (e.g., source structures 120a-120b) and detected by eight simulated detector structures (e.g., detector structures 125a-125h) subsequent to reflection from the simulated tissue. The Monte-Carlo simulations used for generating the simulated reflectance curves for the databases are for a homogeneous tissue model. The simulated tissue for the homogeneous tissue model has homogeneous optical properties from the tissue surface through the epidermis, the dermis, and the subcutaneous tissue. That is, the optical properties of the epidermis, dermis, and subcutataneous are the same for the Monte-Carlo simulations. In the database, each of the simulated reflectance curves is associated with a value for absorption GO and a value for reduced scattering ($\mu_s'$). Each of the simulated reflectance curves in the database can be associated with values for other chromophores.

The database of simulated reflectance curves can include actual values (e.g., floating point values) for simulated reflectances or can include indexed values (e.g., binary values) for the actual values for the simulated reflectances. As shown in FIG. 9, the database includes indexed values (e.g., binary values) for the actual values for the simulated reflectances. The database can include binary words of a variety of lengths dependent, for example, on the accuracy of the entries. The binary words can be 2 bits long, 4 bits long, 8 bits long, 16 bits long, 32 bits long, or other lengths.

In an implementation, one or more mathematical transforms are applied to the simulated reflectance curves prior to entry of the values for the curves into the database. The mathematical transforms can improve the fit of the reflectance data generated by the detector structures to the simulated reflectance curves. For example, a log function can be applied to the simulated reflectance curves to improve the fit of the measured data generated by the detector structures to the simulated reflectance curves.

When an oximetry measurement is made, the reflectance data for each wavelength of emitted light is detected by the detector structures and fitted to the simulated reflectance curves of database 900 individually. For the reflectance data for each wavelength of emitted light fitted to the simulated reflectance curves, the oximeter probe determines absorption $\mu_a$, reduced scattering $\mu_s'$ or both of these values. For example, a first set of reflectance data for a first wavelength of light is fitted to the simulated reflectance curves to determine one or more of absorption $\mu_a$, and reduced scattering $\mu_s'$ (e.g., a first set of tissue parameters). Fitting the reflectance data to the simulated reflectance curves is described further below.

Thereafter, a second set of reflectance data for a second wavelength of light is fitted to the simulated reflectance curves in database 900 to determine one or more of absorption $\mu_a$, and reduced scattering $\mu_s'$ (e.g., a second set of tissue parameters) for the second wavelength. Thereafter, a third set of reflectance data for a third wavelength of light is fitted to the simulated reflectance curves in database 900 to determine one or more of absorption $\mu_a$, and reduced scattering $\mu_s'$ (e.g., a third set of tissue parameters). Thereafter, a fourth set of reflectance data for a fourth wavelength of light is fitted to the simulated reflectance curves in database 900 to determine one or more of absorption $\mu_a$, and reduced scattering $\mu_s'$ (e.g., a fourth set of tissue parameters) for the fourth wavelength.

The four sets of tissue parameters can then be used by the oximeter probe together to determine various values for the tissue, such as oxygenated hemoglobin concentration, deoxygenated hemoglobin concentration, melanin content, or other parameters.

FIG. 10 shows a database 1000 of simulated reflectance curves that is stored in the memory of the oximeter probe in an implementation. The database is for a layered model of tissue (e.g. layered skin). The Monte-Carlo simulations that generated the simulated reflectance curves use the layered tissue model for the simulations. The layered tissue can include two or more layers. In an implementation, the layered tissue includes two layers of tissue. The two layers of tissue have different optical properties, such as different absorption $\mu_a$, reduced scattering $\mu_s'$, or both of these properties.

In one implementation, a first simulated tissue layer is for the epidermis and a second simulated tissue layer is for the dermis. The thickness of the epidermis used in the Monte-Carlo simulations can range from about 40 microns to about 140 microns. For example, the thickness for the epidermis can be 40 microns, 50 microns, 60 microns, 70 microns, 80 microns, 90 microns, 100 microns, 110 microns, 120 microns, 130 microns, 140 microns, or other thickness. The thickness of the dermis used in the Monte-Carlo simulations can range from less than 1 millimeter to an effectively infinite thickness, such as 12 millimeters or greater.

One or more optical properties of the epidermis can be varied when the simulated reflectance curves are generated for the dermis. For example, melanin content can be varied for the epidermis when the simulation reflectance curves are generated for the dermis. Alternatively, $\mu_a$ can be varied for the epidermis when the simulation reflectance curves are generated for the dermis.

In an implementation, database 1000 includes the simulated reflectance curves for the light that is reflected by the combination of the epidermis and the dermis.

The reflectance data for each wavelength of light emitted by the source structures and detected by the detector structures for real tissue measured by the oximeter probe is fit to the simulated reflectance curves one at a time by the processor. Based on the fit to one or more the simulated reflectance curves in the database, the oximeter probe determines one or both of the absorption $\mu_a$ and reduced scattering $\mu_s'$ for the real tissue for one or both layers. From the absorption ($\mu_a$) values determined for one layer, the oximeter probe determines the oxygenated and deoxygenated hemoglobin concentrations for the tissue.

Figure 11A:
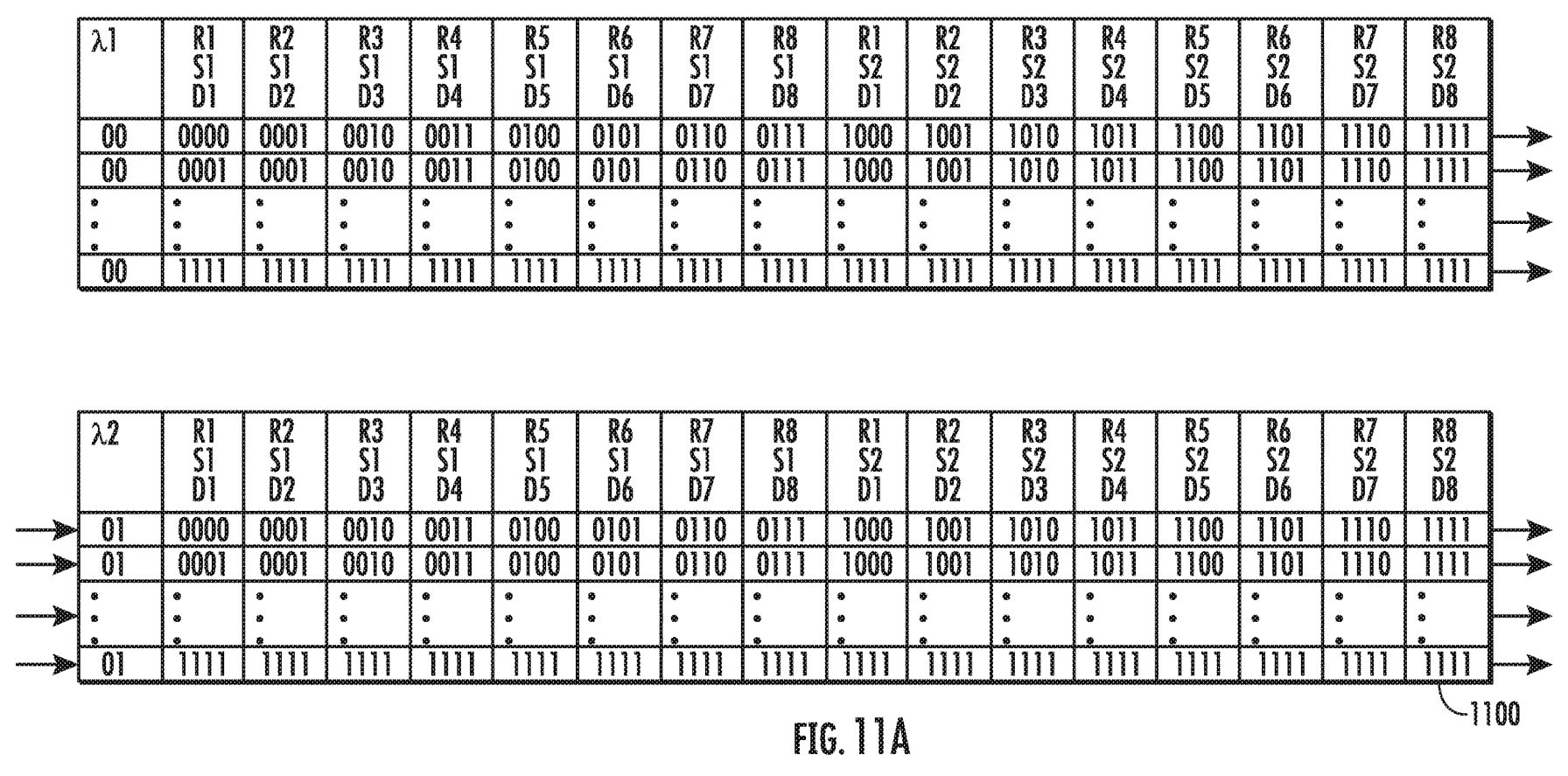
Figure 11B:
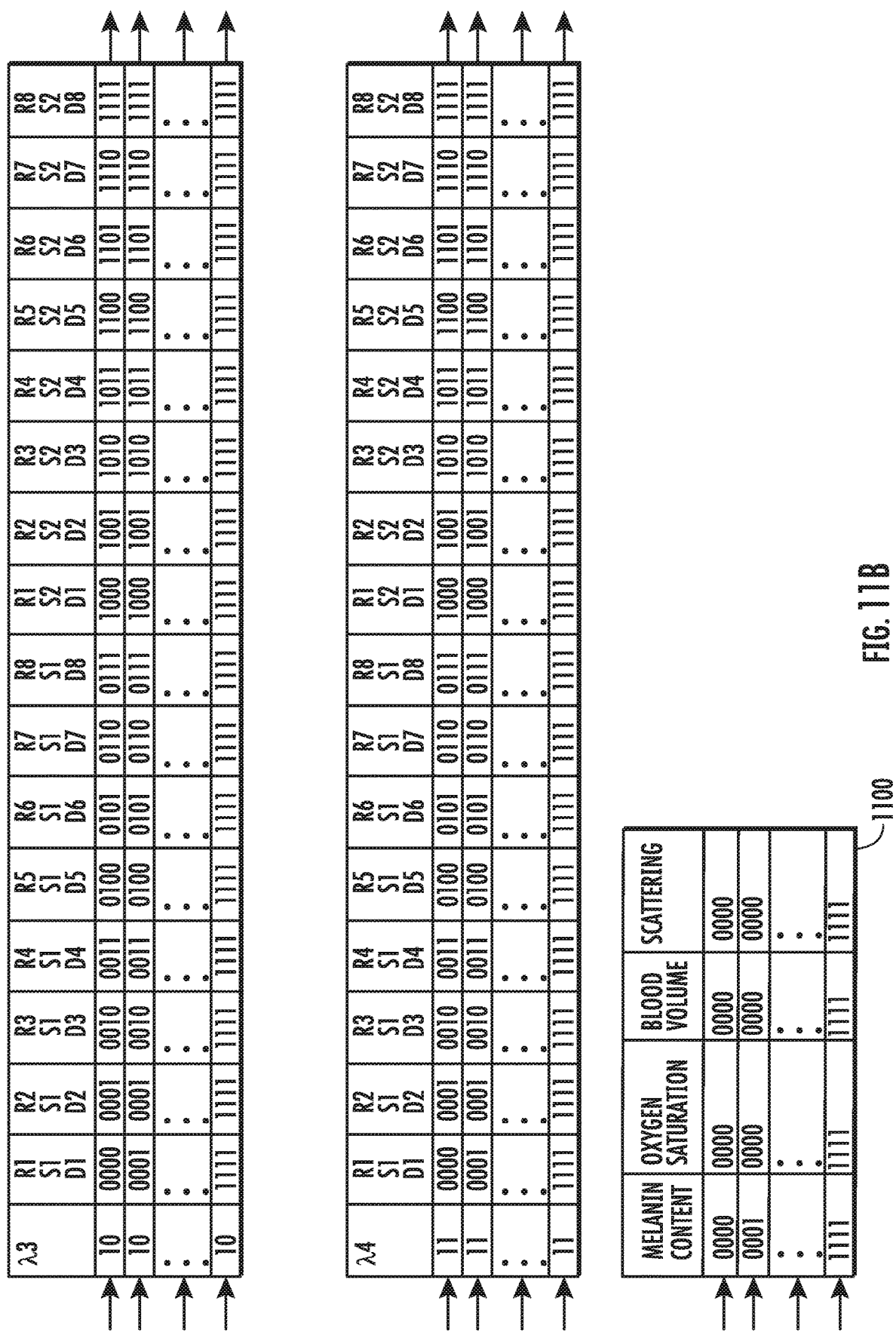

FIGS. 11A-11B show a database 1110 of simulated reflectance curves stored in the memory of the oximeter probe in an implementation. The database is for a layered model of tissue. Each row in the database includes simulated reflectance curves for each of four wavelengths of light emitted from the simulated source structures and detected by simulated detector structures. Each row of four simulated reflectance curves includes 16 values for each simulated reflectance curve. More specifically, each row includes 16 values for the 16 source-to-detector distances for source structures 120a-120b and detector structures 125a-125h. In total, each row includes 64 values for the four simulated reflectance curves for four wavelengths of light emitted from the two simulated source structures and detected by the eight simulated detector structures.

The layered model of tissue for database 1110 can include more or fewer simulated reflectance curves per row if more or fewer wavelengths are emitted from the source structures. Database 1110 can include more or fewer then 16 values for each of simulated reflectance curves if, for example, one or more than two source structure is included in the probe tip, more or fewer detector structures are included in the probe tip, or both.

Each of the four simulated reflectance curves for each row of database 1110 is associated with four tissue parameters, including melanin content, blood volume, scattering, and oxygen saturation (the fraction of oxygenated hemoglobin relative to total hemoglobin for tissue). More of fewer tissue parameters can be included in database 1110.

When a set of detector values that are generated by detector structures 125a-125h for tissue to be measured by the oximeter probe are fit by the processor to one or more of the rows, the oximeter probe thereby determines, in any combination, one or more of the tissue parameters such as melanin content, blood volume, scattering, and oxygen saturation. In an implementation, the oximeter probe is adapted to determine the oxygen saturation for the tissue and display a value for the oxygen saturation on the display.

As described briefly above, database 1110 includes simulated reflectance curves 315 for a layered tissue model. The layers of the simulated tissue can include the epidermis, the dermis, subcutaneous tissue, or any combination of one or more of these layers. The layers can include greater resolution of skin morphology such as the reticular dermis and superficial plexus. The Monte-Carlo simulations that generate the simulated reflectance curve can simulate the tissue for various chromophores included in the tissue layers. For example, the Monte-Carlo simulations can use a tissue model for the epidermis having various melanin contents, but might not use a tissue model for epidermis that includes blood. The Monte-Carlo simulations can use a tissue model for the dermis layer having various blood volumes and various oxygen saturations. In an implementation, the Monte-Carlo simulations do not use a tissue model for dermis that includes melanin. Similarly, the Monte-Carlo simulations can use a tissue model of adipose tissue having various blood volumes and various oxygen saturations. In an implementation, the Monte-Carlo simulations do not use a tissue model for adipose tissue that has melanin. The tissue models for the tissue layers can include concentrations for other tissue chromophores, such as water and fat where the concentrations for these chromophores are relatively typical physiological values.

In an implementation, the various chromophore concentrations that the Monte-Carlo simulations use for generating the simulated reflectance curves span a relatively large and relatively accurate range of actual physiological values present in real tissue. The number of values included in the ranges of actual physiological values can be varied to balance various parameters of tissue oximeter measurements. For example, the number of values used for the range of concentrations of the chromophores in simulated tissue can be relatively high or low and affect the accuracy of measurements made by the oximeter probe. In an implementation, 355 values are used in the Monte-Carlo simulations for the range of melanin content for light absorption in simulated epidermal tissue. In an implementation, 86 values are used in the Monte-Carlo simulations for the range of melanin content for light absorption in simulated dermal tissue. For scattering in both simulated epidermal tissue and simulated dermal tissue, 65 values are used in the Monte-Carlo simulations. In other implementations, the number of these values is different.

Figure 12A:
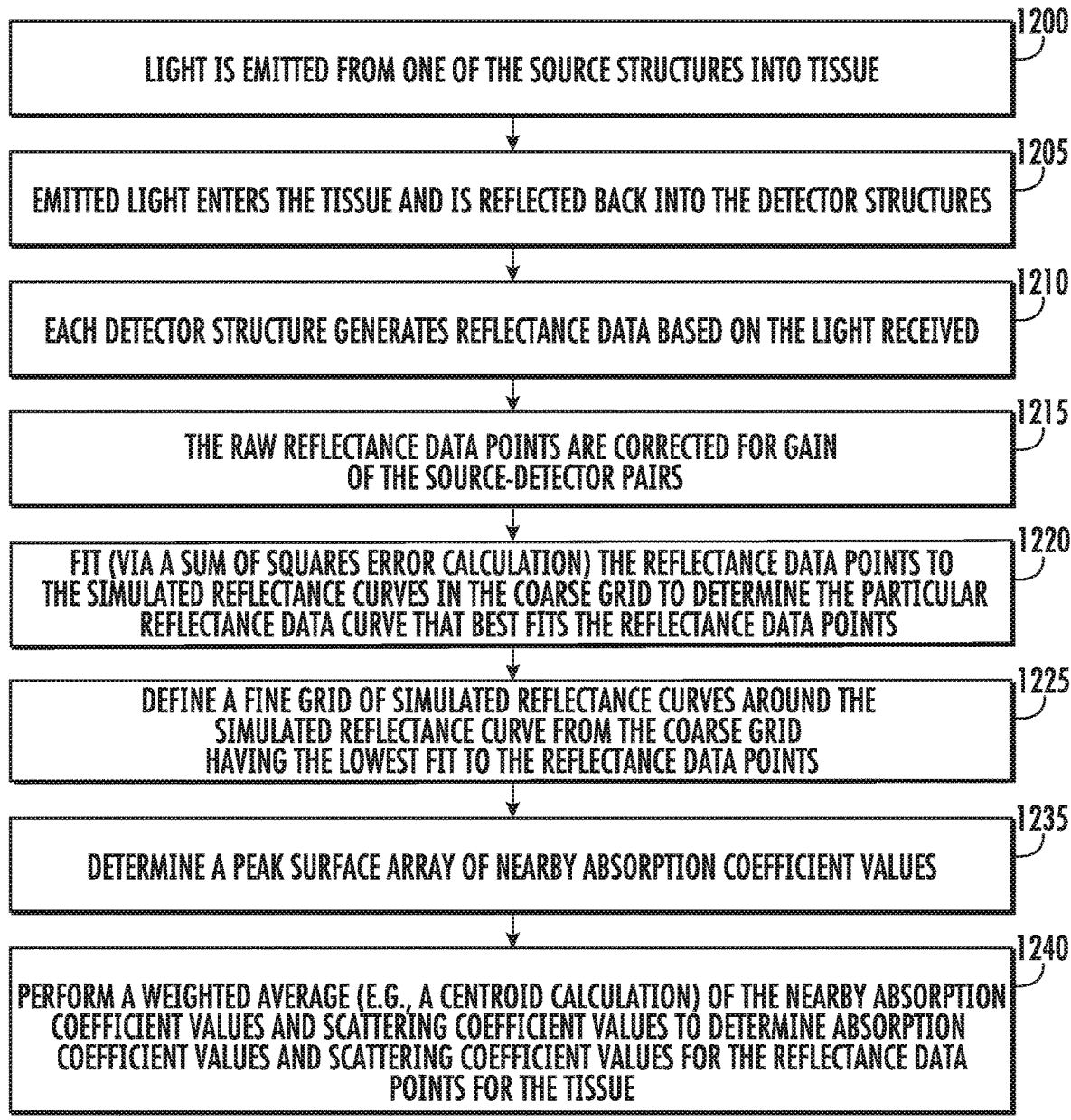
FIGS. 12A-12B show a flow diagram of a method for determining the optical properties of tissue (e.g., real tissue) by the oximeter probe where the oximeter probe uses reflectance data and the simulated reflectance curves to determine the optical properties.
Figure 12B:
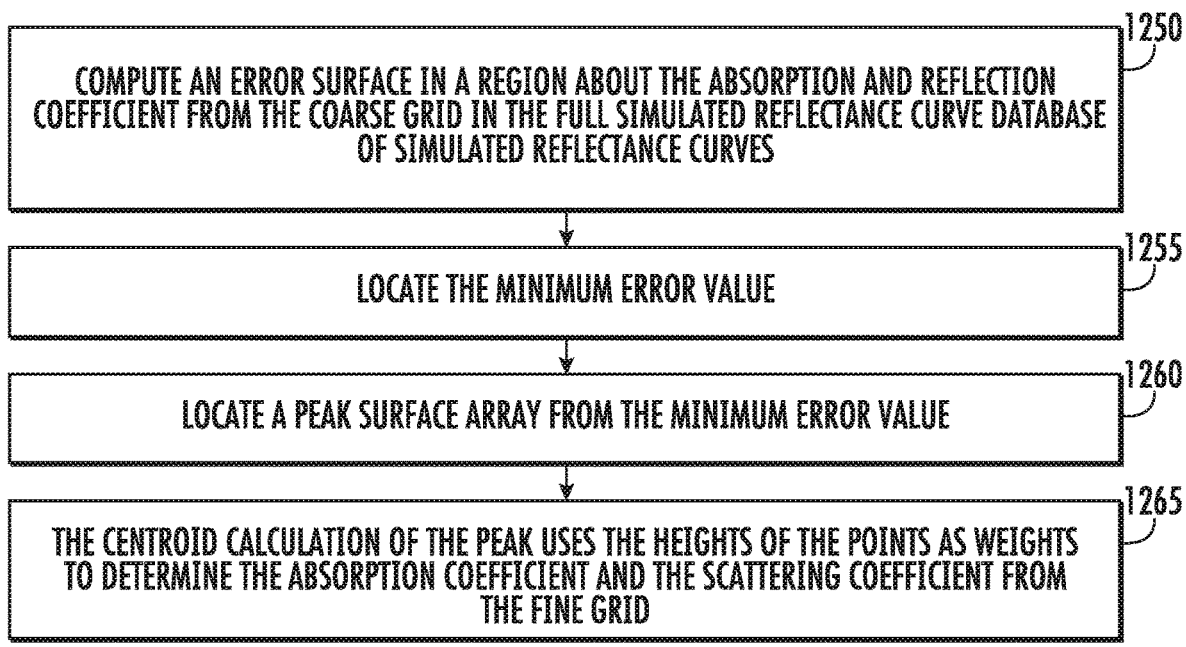

Tissue Analysis. FIGS. 12A and 12B show a flow diagram of a method for determining the optical properties of tissue (e.g., skin) by oximeter probe 101 where the oximeter probe uses reflectance data and simulated reflectance curves 315 to determine the optical properties. The optical properties may include the absorption coefficient $\mu_a$ and the reduced scattering coefficient $\mu_s'$ of the tissue. A further method for conversion of the absorption coefficient $\mu_a$ of the tissue to oxygen saturation values for tissue is described in further detail below. The flow diagram represents one example implementation. Steps may be added to, removed from, or combined in the flow diagram without deviating from the scope of the implementation.

At 1200, oximeter probe 101 emits light (e.g., near infrared light) from one of the source structures 120, such as source structure 120a into tissue. The oximeter probe is generally in contact with the tissue when the light is emitted from the source structure. After the emitted light reflects from the tissue, detector structures 125 detect a portion this light, step 1205, and generate reflectance data points for the tissue, step 1210. Steps 1200, 1205, and 1210 may be repeated for multiple wavelengths of light (e.g., red, near infrared light, or both) and for one or more other source structures, such as source structure 120b. The reflectance data points for a single wavelength might include sixteen reflectance data points if, for example, tissue oximeter probe 115 has sixteen source-to-detector distances. The reflectance data points are sometimes referred to as an N-vector of the reflectance data points.

At 1215, the reflectance data points (e.g., raw reflectance data points) are corrected for gain of the source-detector pairs. During calibration of the source-detector pairs, gain corrections are generated for the source-detector pairs and are stored in memory 117. Generation of the gain corrections is described in further detail below.

At 1220, processor 116 fits (e.g., via a sum of squares error calculation) the reflectance data points to the simulated reflectance curves 315 to determine the particular reflectance data curve that best fits (i.e., has the lowest fit error) the reflectance data points. The database stored in the memory and fit to the reflectance data can be database 900, database 1000, or database 1100. In a specific implementation, a relatively small set of simulated reflectance curves that are a "coarse" grid of the database of the simulated reflectance curves is selected and utilized for fitting step 1220. For example, for database 900 given 39 scattering coefficient values and 150 absorption coefficient $\mu_a$ values, a coarse grid of simulated reflectance curves might be determined by processor 116 by taking every 5th scattering coefficient value and every 8th absorption coefficients $\mu_a$ for a total of 40 simulated reflectance curves in the coarse grid. It will be understood that the foregoing specific values are for an example implementation and that coarse grids of other sizes might be utilized by processor 116. The result of fitting the reflectance data points to the coarse grid is a coordinate in the coarse grid $(\mu_a, \mu_s')_{coarse}$ of the best fitting simulated reflectance curve. For database 1000, the coarse grid will cover absorption in each layer and reduced scattering. Each of the following steps for the method for database 1000 will be adjusted for $\mu_a$ of each layer and $\mu_s'$. For database 1100, the coarse grid will cover melanin content, oxygen saturation, blood volume, and scattering. Each of the following steps for the method for database 1100 will be adjusted for melanin content, oxygen saturation, blood volume, and scattering instead of $\mu_a$ and $\mu_s'$.

At 1225, the particular simulated reflectance curve from the coarse grid having the lowest fit error is utilized by processor 116 to define a "fine" grid of simulated reflectance curves where the simulated reflectance curves in the fine grid are around the simulated reflectance curve from the coarse grid having the lowest fit error.

That is, the fine grid is a defined size, with the lowest error simulated reflectance curve from the coarse grid defining the center of the fine grid. The fine grid may have the same number of simulated reflectance curves as the coarse grid or it may have more or fewer simulated reflectance curves. The fine grid provides a sufficient number of points to determine a peak surface array of nearby absorption coefficient $\mu_a$ values and scattering coefficient $\mu_s'$ values, step 1230, in the fine grid. Specifically, a threshold may be set by processor 116 utilizing the lowest error value from the coarse grid plus a specified offset. The positions of the scattering coefficient $\mu_s'$ and the absorption coefficient $\mu_a$ on the fine grid that have errors below the threshold may all be identified for use in determining the peak surface array for further determining the scattering coefficient $\mu_s'$ and the absorption coefficient $\mu_a$ for the reflectance data. Specifically, an error fit is made for the peak to determine the absorption coefficient $\mu_a$ and the scattering coefficient $\mu_s'$ values at the peak. A weighted average (e.g., a centroid calculation) of the absorption coefficient $\mu_a$ and the scattering coefficient $\mu_s'$ values at the peak may be utilized by the oximeter probe for the determination of the absorption coefficient $\mu_a$ and the scattering coefficient $\mu_s'$ values for the reflectance data points for the tissue, step 1240.

Weights for the absorption coefficient $\mu_a$ and the scattering coefficient $\mu_s'$ values for the weighted average may be determined by processor 116 as the threshold minus the fine grid error. Because points on the fine grid are selected with errors below the threshold, this gives positive weights. The weighted calculation of the weighted average (e.g., centroid calculation) renders the predicted scattering coefficient $\mu_s'$ and absorption coefficient $\mu_a$ (i.e., $(\mu_a, \mu_s')_{fine}$) for the reflectance data points for the tissue. Other methods may be utilized by the oximeter probe, such as fitting with one or more of a variety of nonlinear least squares to determine the true minimum error peak for the absorption coefficient $\mu_a$.

In an implementation, processor 116 calculates the log of the reflectance data points and the simulated reflectance curves, and divides each log by the square root of the source-to-detector distances (e.g., in centimeters). These log values divided by the square root of the of the source-to-detector distances may be utilized by processor 116 for the reflectance data points and the simulated reflectance curves in the foregoing described steps (e.g., steps 1215, 1220, 1225, and 1230) to improve the fit of the reflectance data points to the simulated reflectance curves.

According to another implementation, the offset is set essentially to zero, which effectively gives an offset of the difference between the coarse grid minimum and the fine grid minimum. The method described above with respect to FIG. 12A relies on minimum fit error from the coarse grid, so the true minimum error on the fine grid is typically lower. Ideally, the threshold is determined from the lowest error on the fine grid, which would typically require additional computation by the processor.

The following is a further detailed description for finding the particular simulated reflectance curve that best fits the reflectance data points in the fine grid in an implementation. FIG. 12B shows a flow diagram of a method for finding the particular simulated reflectance curve that best fits the reflectance data points in the fine grid in an implementation. The flow diagram represents one example implementation. Steps may be added to, removed from, or combined in the flow diagram without deviating from the scope of the implementation.

Subsequent to determining the particular simulated reflectance curve $(\mu_a, \mu_s')_{coarse}$ from the coarse grid that best fits the reflectance data points at step 1225, processor 116 computes an error surface in a region about $(\mu_a, \mu_s')_{coarse}$ in the full simulated reflectance curve database (i.e., 16×5850 $(\mu_a, \mu_s')$ database) of simulated reflectance curves, step 1250. The error surface is denoted as: $err(\mu_a, \mu_s')$. Thereafter, processor 116 locates the minimum error value in $err(\mu_a, \mu_s')$, which is referred to as $err_{min}$, step 1255. Processor 116 then generates a peak surface array from $err(\mu_a, \mu_s')$ that is denoted by $pksurf(\mu_a, \mu_s')=k+err_{min}-err(\mu_a, \mu_s')$ if the peak surface is greater than zero, or $pksurf(\mu_a, \mu_s')=k+err_{min}-err(\mu_a, \mu_s')=0$ if the peak surface is less than or equal to zero, step 1260. In the expression k is chosen from a peak at the minimum point of $err(\mu_a, \mu_s')$ with a width above zero of approximately ten elements. The center-of-mass (i.e., the centroid calculation) of the peak in $pksurf(\mu_a, \mu_s')$ uses the heights of the points as weights, step 1265. The position of the center-of-mass is the interpolated result for the absorption coefficient $\mu_a$ and the scattering coefficient $\mu_s'$ for the reflectance data points for the tissue.

The method described above with respect to FIGS. 12A and 12B for determining the absorption coefficient $\mu_a$ and the scattering coefficient $\mu_s'$ for reflectance data points for tissue may be repeated for each of the wavelengths (e.g., 3 or 4 wavelengths) generated by each of source structures 120.

Oxygen Saturation Determination. According to a first implementation, processor 116 determines the oxygen saturation for tissue that is probed by oximeter probe 101 by utilizing the absorption coefficients $\mu_a$ (e.g., 3 or 4 absorption coefficients $\mu_a$) that are determined (as described above) for the 3 or 4 wavelengths of light that are generated by each source structure 120. According to a first implementation, a look-up table of oxygen saturation values is generated for finding the best fit of the absorption coefficients $\mu_a$ to the oxygen saturation. The look-up table may be generated by assuming a range of likely total hemoglobin, melanin, and oxygen saturation values and calculating $\mu_a$ for each of these scenarios. Then, the absorption coefficient $\mu_a$ points are converted to a unit vector by dividing by a norm of the unit vector to reduce systematic error and only depend on relative shape of curve. Then the unit vector is compared to the look-up table to find the best fit, which gives the oxygen saturation.

According to a second implementation, processor 116 determines the oxygen saturation for the tissue by calculating the net analyte signal (NAS) of deoxygenated hemoglobin and oxygenated hemoglobin. The NAS is defined as the portion of the spectrum that is orthogonal to the other spectral components in the system. For example, the NAS of a deoxygenated hemoglobin in a system that also contains oxygenated hemoglobin and deoxygenated hemoglobin is the portion of the spectrum that is orthogonal to the oxygenated hemoglobin spectrum and the melanin spectrum. The concentrations of deoxygenated and oxygenated hemoglobin can be calculated by vector multiplying the respective NAS by the previously determined absorption coefficients at each wavelength. Oxygen saturation is then readily calculated as the concentration of oxygenated hemoglobin divided by the sum of oxygenated hemoglobin and deoxygenated hemoglobin. Anal. Chem. 58:1167-1172 (1986) by Lorber is incorporated by reference herein and provides a framework for a further detailed understanding of the second implementation for determining the oxygen saturation for the tissue.

In an implementation of oximeter probe 101, the reflectance data is generated by detector structures 125 at 30 Hertz, and oxygen saturation values are calculated at approximately 3 Hertz. A running average of determined oxygen saturation values (e.g., at least three oxygen saturation values) may be displayed on display 115, which might have an update rate of 1 Hertz.

Optical Properties. As described briefly above, each simulated reflectance curve 315 that is stored in memory 117 represents unique optical properties of tissue. More specifically, the unique shapes of the simulated reflectance curves, for a given wavelength, represent unique values of the optical properties of tissue, namely the scattering coefficient ($\mu_s$), the absorption coefficient ($\mu_a$), the anisotropy of the tissue (g), and index of refraction of the tissue from which the tissue properties may be determined.

The reflectance detected by detector structures 125 for relatively small source-to-detector distances is primarily dependent on the reduced scattering coefficient, $\mu_s'$. The reduced scattering coefficient is a "lumped" property that incorporates the scattering coefficient $\mu_s$ and the anisotropy g of the tissue where $\mu_s'=\mu_s(1-g)$, and is used to describe the diffusion of photons in a random walk of many steps of size of $1/\mu_s'$ where each step involves isotropic scattering. Such a description is equivalent to a description of photon movement using many small steps $1/\mu_s$ which each involve only a partial deflection angle if there are many scattering events before an absorption event, i.e., $\mu_a \ll \mu_s'$.

In contrast, the reflectance that is detected by detector structures 125 for relatively large source-to-detector distances is primarily dependent on the effective absorption coefficient $\mu_{\textit{eff}}$ which is defined as $\sqrt{3\mu_a(\mu_a+\mu s')}$ which is a function of both $\mu_a$ and $\mu_s'$.

Thus, by measuring reflectance at relatively small source-to-detector distances (e.g., S1-D4 and S2-D8 of FIG. 2) and relatively large source-to-detector distances (e.g., S1-D8 and S2-D4 of FIG. 2), both $\mu_a$ and $\mu_s'$ can be independently determined from one another. The optical properties of the tissue can in turn provide sufficient information for the calculation of oxygenated hemoglobin and deoxygenated hemoglobin concentrations and hence the oxygen saturation of the tissue.

Figure 13:
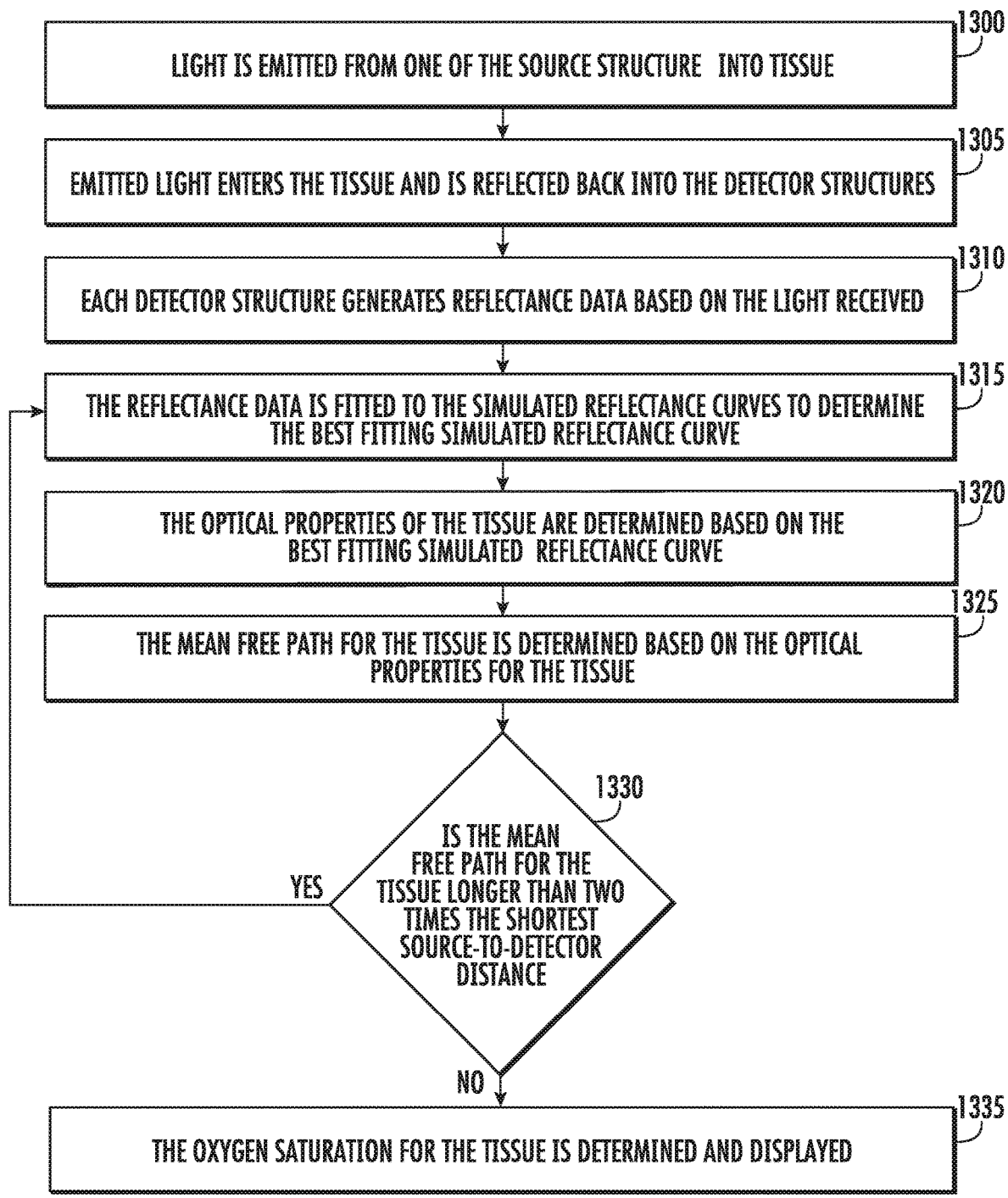
FIG. 13 shows a flow diagram of another method for determining the optical properties of tissue by the oximeter probe.

Iterative Fit for Data Collection Optimization. FIG. 13 shows a flow diagram of another method for determining the optical properties of tissue by oximeter probe 101. The flow diagram represents one example implementation. Steps may be added to, removed from, or combined in the flow diagram without deviating from the scope of the implementation.

At 1300, oximeter probe 101 emits light (e.g., near infrared light) from one of the source structures, such as source structure 120*a* into tissue. After the emitted light reflects from the tissue, detector structures 125 detect the light, step 1305, and generate reflectance data for the tissue, step 1310. Steps 1300, 1305, and 1310 may be repeated for multiple wavelengths of light and for one or more other source structures, such as source structure 120*b*. At 1315, oximeter probe 101 fits the reflectance data to simulated reflectance curves 315 and determines the simulated reflectance curve to which the reflectance data has the best fit. The database stored in the memory and fit to the reflectance data can be database 900, database 1000, or database 1100. Thereafter, oximeter probe 101 determines the optical properties (e.g., $\mu_a$, and $\mu_s'$ for database 900 or database 1000, or melanin content, oxygen saturation, blood volume, and scattering for database 1100) for the tissue based on the optical properties of the simulated reflectance curve that best fits the reflectance data, step 1320.

At 1325 oximeter probe 101 determines the mean free path of the light in the tissue from the optical properties (e.g., mfp=$1/(\mu_a+\mu_s')$) determined at step 1320. Specifically, the mean free path can be determined from the optical properties obtained from a cumulative reflectance curve that includes the reflectance data for all of the source-detector pairs (e.g., pair 1: source structure 120*a* and detector structure 125*a*; pair 2: source structure 120*a* and detector structure 125*b*; pair 3: source structure 120*a* and detector structure 125*c*; pair 4: source structure 120*a* and detector structure 125*d*; pair 5: source structure 120*a* and detector structure 125*e*; pair 6: source structure 120*a* and detector structure 125*f*; pair 7: source structure 120*a* and detector structure 125*g*; pair 8: source structure 120*a* and detector structure 125*h*; pair 9: source structure 120*b* and detector structure 125*a*, pair 10: source structure 120*b* and detector structure 125*b* . . . and others).

At 1330, oximeter probe 101 determines whether the mean free path calculated for a given region of the tissue is longer than two times the shortest source-to-detector distance (e.g., S1-D4 and S2-D8 of FIG. 2). If the mean free path is longer than two times the shortest source-to-detector distance, then the collected reflectance data is refitted to the simulated reflectance curves (i.e., reanalyzed) without utilizing the reflectance data collected from the detector structures for the source-to-detector pairs having the shortest source-to-detector distance. For example, steps 1315-1330 are repeated without use of the reflectance data from detector structure 125e with source structure 120a acting as the source for detector structure 125d, and without use of the reflectance data from detector structure 125h with source structure 120b acting as the source for detector structure 125h. The process of calculating the mean free path and discarding the reflectance data for one or more source-detector pairs may be repeated until no source-detector pairs that contribute reflectance data to the fit have a source-to-detector distance shorter than one half of the calculated mean free path. Thereafter, oxygen saturation is determined from the best fitting simulated reflectance curve and reported by oximeter probe 101, such as on display 115, step 1335.

Light that is emitted from one of the source structures 120 into tissue and that travels less than half of the mean free path is nondiffusely reflected or approximately nondiffusely reflected (e.g., can have a diffuse reflection element). The re-emission distance for this light is strongly dependent on the tissue phase function and the local tissue composition. Therefore, using the reflectance data for this light tends to result in a less accurate determination of the optical properties and tissue properties as compared with the reflectance data for light that has undergone multiple scattering events.

Data Weighting Detector Structures. Detector structures 125 that are positioned at increasing distances from source structures 120 receive decreasing amounts of reflectance from tissue. Therefore, the reflectance data generated by detector structures 125 having relatively short source-to-detector distances (e.g., S1-D8 and S2-D8 of FIG. 2) tends to exhibit intrinsically higher signal compared to reflectance data generated by detector structures having relatively long source-to-detector distances (e.g., S1-D8 and S2-D4 of FIG. 2). Fit algorithms may therefore preferentially fit the simulated reflectance curves to the reflectance data that is generated by detector structures 125 having relatively short source-to-detectors distances (e.g., source-to-detector distances less than or equal to the average distance between the source structures and the detector structures) more tightly than reflectance data that is generated by detector structures having relatively long source-to-detector distances (e.g., source-to-detector distances greater than the average distance). For relatively accurate determination of the optical properties from the reflectance data, this distance-proportional skew may be undesirable and may be corrected by weighting the reflectance data as described immediately below.

Figure 14:
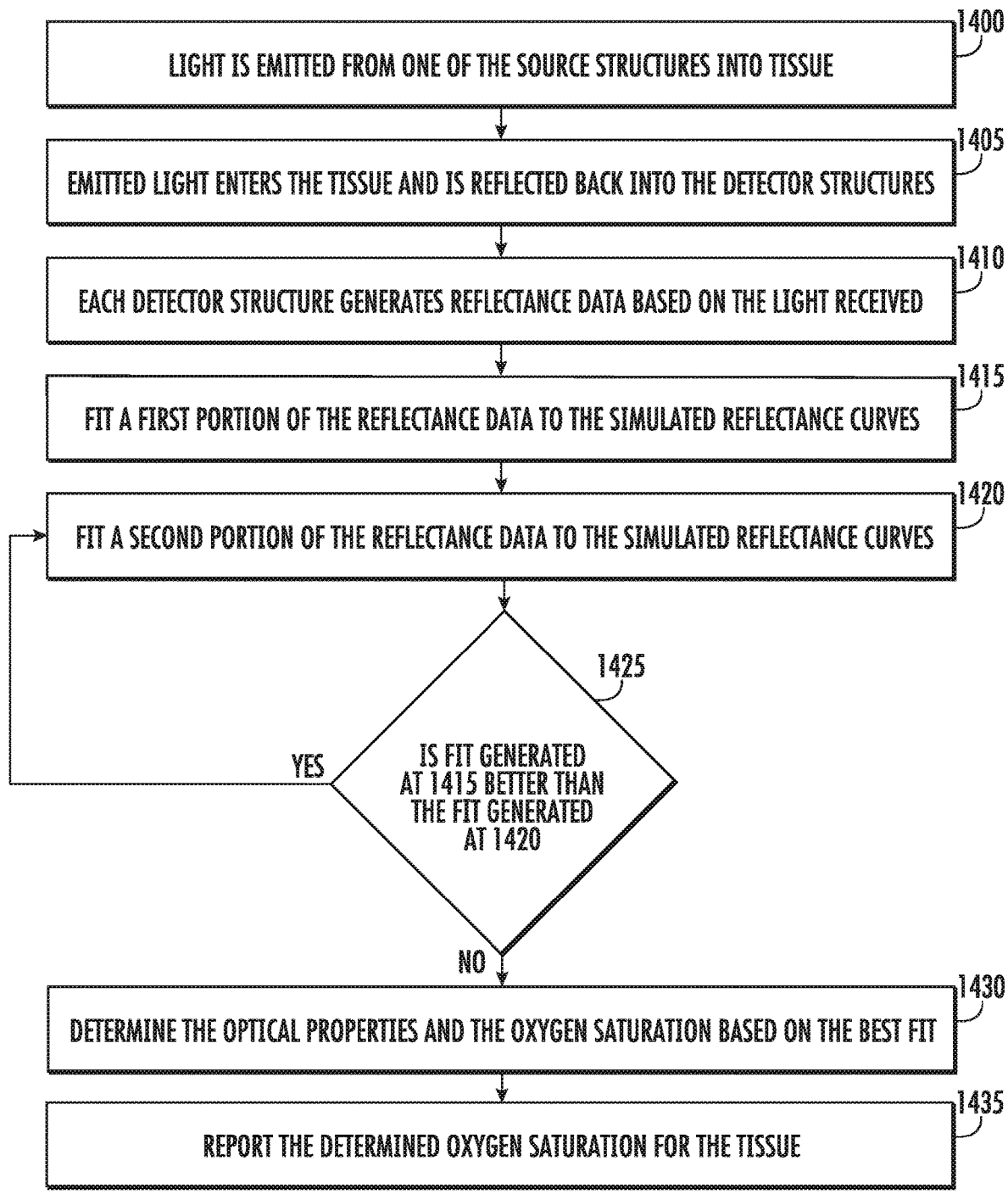
FIG. 14 shows a flow diagram of a method for weighting reflectance data generated by select detector structures.

FIG. 14 shows a flow diagram of a method for weighting reflectance data generated by select detector structures 125. The flow diagram represents one example implementation. Steps may be added to, removed from, or combined in the flow diagram without deviating from the scope of the implementation.

At 1400, oximeter probe 101 emits light from one of the source structures, such as source structure 120a into tissue. After the emitted light reflects from the tissue, detector structures 125 detect the light, step 1405, and generate reflectance data for the tissue, step 1410. Steps 1400, 1405, and 1410 may be repeated for multiple wavelengths of light and for one or more other source structures, such as source structure 120b. At 1415, oximeter probe 101 fits a first portion of the reflectance data to the simulated reflectance curves 315. The database stored in the memory and fit to the reflectance data can be database 900, database 1000, or database 1100. The first portion of the reflectance data is generated by a first portion of detector structures that are less than a threshold distance from the source structure. The threshold distance may be the average distances (e.g., approximate midrange distance) between the source structures and the detector structures. At 1420, reflectance data for a second portion of the reflectance data is fitted to the simulated reflectance curves. The second portion of reflectance data is generated by the first portion of the detector structures and another detector structure that is at the next largest source-to-detector distance from the source compared to the threshold distance. For example, if the first portion of detector structures includes detector structures 125c, 125d, 125e, and 125f, then the detector structure that is at the next largest source-to-detector distance is detector structure 125g (see Table 1).

At 1425, the fit generated at step 1415 is compared to the fit generated at step 1420 to determine whether the fit generated at step 1420 is better than the fit generated at 1415. As will be understood by those of skill in the art, a "closeness" of a fit of data to a curve is quantifiable based on a variety of parameters, and the closeness of fits are directly comparable to determine the data having a closer fit (closer fit) to a curve. As will be further understood, a closer fit is sometimes also referred to as a better fit or a tighter fit. If the fit generated at step 1420 is better than the fit generated at step 1415, then steps 1420 and 1425 are repeated with reflectance data that is generated by detector structures that include an additional detector structure (according to the example being considered, detector structure 125c) that is positioned at a next increased source-to-detector distance from the source. Alternatively, if the fit generated at step 1420 is not better than the fit generated at step 1415, then the reflectance data for detector structures 125 that are positioned at source-to-detector distances that are greater than the threshold distance are not used in the fit. Thereafter, oximeter probe 101 uses the fit generated at 1415 or step 1420 (if better than the fit determined at step 1415) to determine the optical properties and the oxygen saturation of the tissue, step 1430. Thereafter, oxygen saturation is reported by oximeter probe 101, such as on display 115, step 1435.

According to an alternative implementation, if the fit generated at step 1420 is not better than the fit generated at step 1415, then the reflectance data are weighted by a weighting factor for detector structures that have source-to-detector distances that are greater than the threshold distance so that this weighted reflectance data has a decreased influence on the fit. Reflectance data that is not used in a fit may be considered as having a zero weight and may be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the detector structures, and the amount of noise can scale as the square root of the magnitude of the reflectance data.

According to a further implementation, oximeter probe 101 iteratively weights the reflectance data based on the amount of noise associated with the measurements of the reflectance data. Specifically, the reflectance data generated by detector structures having relatively large source-todetector distances generally have lower signal-to-noise ratio compared to the reflectance data generated by detector structure having relatively short source-to-detector distances. Weighting the reflectance data generated by detector structures having relatively large source-to-detector distances allows for this data to contribute to the fit equally or approximately equally to other reflectance data.

Methods described for matching reflectance data to a number of Monte-Carlo-simulated reflectance curves provide for relatively fast and accurate determination of the optical properties of real tissue probed by the oximeter probe. Speed in determining optical properties of tissue is an important consideration in the design of intraoperative probes compared to postoperative probes. Further, the Monte-Carlo methods described allow for robust calibration methods that in-turn allow for the generation of absolute optical properties as compared with relative optical properties. Reporting absolute optical properties, as opposed to relative optical properties, is relatively important for intra-operative oximeter probes as compared with post-operative oximeter probes.

This description of the invention has been presented for the purposes of illustration and description. It is not intended to be exhaustive or to limit the invention to the precise form described, and many modifications and variations are possible in light of the teaching above. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. A method comprising:
contacting an oximeter probe of an oximeter device to a target tissue of a patient;
transmitting first light at a first time from a source structure of the oximeter probe into the target tissue;
detecting first reflected light that is reflected from the target tissue by a plurality of detector structures of the oximeter probe;
generating by the detector structures first reflectance data for the first reflected light detected by the plurality of detector structures;
fitting the first reflectance data to a plurality of simulated reflectance curves;
determining one or more best fitting ones of the simulated reflectance curves from the fit of the first reflectance data to the plurality of simulated reflectance curves, wherein each of the simulated reflectance curves is associated with a value for an oximeter parameter;
determining at least a first oximeter parameter for the one or more best fitting ones of the simulated reflectance curves to the first reflectance data;
determining, by a processor of the oximeter device, a first value for a first oximeter measurement based on the first oximeter parameter;
storing the first value, which is determined by the processor, for the first oximeter measurement in a memory;
transmitting second light at a second time from the source structure of the oximeter probe into the target tissue;
detecting second reflected light that is reflected from the target tissue by the plurality of detector structures of the oximeter probe;
generating by the detector structures second reflectance data for the second reflected light detected by the plurality of detector structures;
fitting the second reflectance data to the plurality of simulated reflectance curves;
determining one or more best fitting ones of the simulated reflectance curves from the fit of the second reflectance data to the plurality of simulated reflectance curves;
determining at least a second oximeter parameter for the one or more best fitting ones of the simulated reflectance curves to the second reflectance data;
determining, by the processor of the oximeter device, a second value for a second oximeter measurement based on the second oximeter parameter;
retrieving, by the processor of the oximeter device, the first value from the memory;
determining, by the processor of the oximeter device, a percentage difference between the first and second value; and
displaying the percentage difference, which is determined by the processor, on a display of the oximeter probe.

2. The method of claim 1 wherein the first oximeter measurement is a first oxygen saturation and the second oximeter measurements is a second oxygen saturation.

3. The method of claim 1 wherein the percentage difference is displayed as a numerical value.

4. The method of claim 1 comprising displaying the second value on the display.

5. The method of claim 1 comprising displaying an arrow on the display pointing in a downward direction to indicate the percentage difference has increased.

6. The method of claim 4 wherein the arrow is red.

7. The method of claim 1 comprising displaying an arrow on the display pointing in an upward direction to indicate the percentage difference has decreased.

8. The method of claim 5 wherein the arrow is green.

9. The method of claim 1 comprising introducing epinephrine into the target tissue; and
determining an effect of the epinephrine in the target tissue via change in the percentage value displayed on the display.

10. A method comprising:
contacting an oximeter probe of an oximeter device to a first target tissue of a patient;
transmitting first light at a first time period from a source structure of the oximeter probe into the first target tissue;
detecting first reflected light that is reflected from the first target tissue by a plurality of detector structures of the oximeter probe;
generating by the detector structures first reflectance data for the first reflected light detected by the plurality of detector structures;
fitting the first reflectance data to a plurality of simulated reflectance curves;
determining one or more best fitting ones of the simulated reflectance curves from the fit of the first reflectance data to the plurality of simulated reflectance curves, wherein each of the simulated reflectance curves is associated with a value for an oximeter parameter;
determining, by the processor of the oximeter device, at least a first value for a first oximeter measurement for the one or more best fitting ones of the simulated reflectance curves to the first reflectance data, wherein the first value can be changed by the processor for subsequent first light measurements;

storing the first value, which is determined by the processor, for the first oximeter measurement in a memory;

transmitting second light at a second time period from the source structure of the oximeter probe into second target tissue of the patient;

detecting second reflected light that is reflected from the second target tissue by the plurality of detector structures of the oximeter probe;

generating by the detector structures second reflectance data for the second reflected light detected by the plurality of detector structures;

fitting the second reflectance data to the plurality of simulated reflectance curves;

determining one or more best fitting ones of the simulated reflectance curves from the fit of the second reflectance data to the plurality of simulated reflectance curves;

determining, by the processor of the oximeter device, at least a second value for a second oximeter measurement for the one or more best fitting ones of the simulated reflectance curves to the second reflectance data;

retrieving, by the processor of the oximeter device, the first value from the memory;

determining, by the processor of the oximeter device, a percentage difference between the first and second value; and displaying the percentage difference, which is determined by the processor, on a display of the oximeter probe if the percentage difference is greater than a threshold percentage difference.

11. The method of claim 10 comprising transmitting third light at a third time period from the source structure of the oximeter probe into third target tissue of the patient;

detecting third reflected light that is reflected from the third target tissue by the plurality of detector structures of the oximeter probe;

generating by the detector structures third reflectance data for the third reflected light detected by the plurality of detector structures;

fitting the third reflectance data to the plurality of simulated reflectance curves;

determining one or more best fitting ones of the simulated reflectance curves from the fit of the third reflectance data to the plurality of simulated reflectance curves;

determining at least a third oximeter parameter for the one or more best fitting ones of the simulated reflectance curves to the third reflectance data;

determining, by the processor of the oximeter device, a third value for a third oximeter measurement based on the third oximeter parameter;

retrieving, by the processor of the oximeter device, the first value from the memory;

determining, by the processor of the oximeter device, the percentage difference between the first and third value; and displaying the percentage difference between the first and third value, which is determined by the processor, on a display of the oximeter probe if the percentage difference is greater than a threshold percentage difference.

12. The method of claim 11 wherein the first and second tissue are at the same location.

13. The method of claim 11 wherein the first and second tissue are at the same location and the third tissue is at a different location.

14. The method of claim 11 wherein the first, second, and third tissue are at the same location.

15. The method of claim 10 wherein the first and second tissue are at different locations.

16. The method of claim 10 comprising adjusting the percentage difference between the first and second values based on a melanin concentration of the first target tissue of a patient.

17. The method of claim 16 comprising adjusting the percentage difference between the first and third values based on the melanin concentration of the target tissue of a patient.

18. The method of claim 10 wherein the percentage difference is a relative oxygen saturation value for a first oxygen saturation value and a second oxygen saturation value.

19. The method of claim 18 wherein the relative oxygen saturation value is unavailable for display until after the second time period and after the second oxygen saturation value has been determined.

20. The method of claim 10 comprising adjusting the percentage difference between the first and second values based on a melanin concentration of the second target tissue of a patient.

* * * * *